US007105318B2

(12) United States Patent
Kessler et al.

(10) Patent No.: US 7,105,318 B2
(45) Date of Patent: Sep. 12, 2006

(54) SPECIFIC AND SENSITIVE NUCLEIC ACID DETECTION METHOD

(75) Inventors: Christoph Kessler, Icking (DE); Gerd Haberhausen, Iffeldorf (DE); Knut Bartl, Wielenbach (DE); Henrik Orum, Vaerlose (DK)

(73) Assignee: Roche Diagnostics GmbH, Penzberg (DE)

( * ) Notice: Subject to any disclaimer, the term of this patent is extended or adjusted under 35 U.S.C. 154(b) by 516 days.

(21) Appl. No.: 10/322,138

(22) Filed: Dec. 17, 2002

(65) Prior Publication Data

US 2003/0175765 A1 Sep. 18, 2003

Related U.S. Application Data

(62) Division of application No. 09/530,746, filed as application No. PCT/EP98/06952 on Nov. 3, 1998, now abandoned.

(30) Foreign Application Priority Data

| Nov. 4, 1997 | (DE) | ................... 197 48 690 |
| Mar. 28, 1998 | (DE) | ................... 198 14 001 |
| Apr. 2, 1998 | (DE) | ................... 198 14 828 |

(51) Int. Cl.
C12P 19/34 (2006.01)
C12Q 1/68 (2006.01)
C07H 21/02 (2006.01)
C07H 21/04 (2006.01)

(52) U.S. Cl. .................. 435/91.2; 435/6; 536/23.1; 536/24.3; 536/24.32

(58) Field of Classification Search ............. None
See application file for complete search history.

(56) References Cited

U.S. PATENT DOCUMENTS

| 4,683,202 | A | 7/1987 | Mullis |
| 5,200,313 | A | 4/1993 | Carrico |
| 5,453,355 | A | * | 9/1995 | Birkenmeyer et al. ......... 435/6 |
| 5,527,898 | A | 6/1996 | Bauer et al. |
| 5,538,848 | A | 7/1996 | Livak et al. |
| 5,858,671 | A | 1/1999 | Jones |
| 5,882,857 | A | 3/1999 | Western |
| 5,948,648 | A | 9/1999 | Kahn et al. |
| 6,154,707 | A | 11/2000 | Livak et al. |
| 6,245,514 | B1 | 6/2001 | Wittwer |

FOREIGN PATENT DOCUMENTS

| EP | 0 070 685 A2 | 1/1983 |
| EP | 0 229 701 A2 | 7/1987 |
| EP | 0 202 362 | 4/1989 |
| EP | 0 787 807 | 8/1992 |
| EP | 0 593 789 A | 4/1994 |
| EP | 0 329 822 | 6/1994 |
| WO | WO 91/01384 | 2/1991 |
| WO | WO 91/10675 | 7/1991 |
| WO | WO 92/02638 | 2/1992 |
| WO | WO 92/19743 | 11/1992 |
| WO | WO 94/03635 | 2/1994 |
| WO | WO 95/02690 | 1/1995 |
| WO | WO 96/29431 | 9/1996 |
| WO | WO 96/35437 | 11/1996 |

OTHER PUBLICATIONS

Nedjar, S. et al., "Simultaneous Amplification and Detection of Specific Hepatitis B Virus and Hepatitis C Virus Genomic Sequences in Serum Samples", J. Med. Virol., vol. 42, pp. 212-216 (1994).*
Nedjar, S. et al., "Co-amplification of specific sequences of HCV and HIV-1 genomes by using the polymerase chain reaction assay: a potential tool for the simultaneous detection of HCV and HIV-1", J. Virol. Meth., vol. 35, pp. 297-304 (1991).*
Garson, J.A. et al., "Improvement of HCV genome detection with "short" PCR products", Lancet, vol. 338, pp. 1466-1467 (1991).*
Scottstedt, V. et al., "PCR-Routine-Screening auf HBV-,HCV- und HIV-1-Genom in einem grossen Blutspendedienst-Erfahrungen und erste Ergebnisse", Beitr. Infusionsther. Transfusionsmed., vol. 34, pp. 21-25 (1997).*
Chelly et al., "Dystrophin gene transcribed from different promoters in neuronal and glia cells", Nature (1990) 344:64-5.
Dieffenbach et al., "PCR Primer, A Laboratory Manual", (1995) 133-142.
Rychlik et al., "Optimization of the annealing temperature for DNA Amplification *in vitro*", Nucleic Acids Research, (1990) 18:6409-6412.
Sommer et al., "Minimal homology requirements for PCR primers", Nucleic Acids Research, (1989) 17:6749.
Leary, T.P., et al., "Sequence and Genomic Organization of GBV-C: A Novel Member of the Flaviviridae Associated with Human Non-A-E Hepatitis," (1996), J. Med. Virol., 48(1), pp. 60-67.
Muerhoff, A.S., et al., "Genomic Organization of GB Viruses A' and B: Two new Members of the Flaviviridae Associated with GB Agent Hepatitis," (1995), J. Virol., 69(9), pp. 5621-5630.

(Continued)

*Primary Examiner*—Teresa Strzelecka
(74) *Attorney, Agent, or Firm*—Townsend and Townsend and Crew LLP; Jean M. Lockyer; Matthew E. Hinsch

(57) ABSTRACT

Method for the detection of a nucleic acid comprising the production of a plurality of amplificates of a section of this nucleic acid with the aid of two primers, one of which can bind to a binding sequence A of the nucleic acid and the other can bind to a binding sequence C' which is complementary to a sequence C which is located in the 3' direction from A and does not overlap with A, contacting the amplificates with a probe having a binding sequence D which can bind to a sequence B which is located between the sequences A and C or to the complement thereof, and detecting the formation of a hybrid of the amplificate and probe where the sequence located between the binding sequences A and C contains no nucleotides that do not belong to the binding sequence D of the probe or its complement D'.

7 Claims, 8 Drawing Sheets

OTHER PUBLICATIONS

Simons, J.N., et al., "Identification of Two Flavivirus-like Genomes in the GB Hepatitis Agent," (1995), *PNAS USA*, 92, pp. 3401-3405.

Walker, G.T., et al., "Isothermal *in vitro* Amplification of DNA by a Restriction Enzyme/DNA Polymerase System," (1992), *PNAS*, 89, pp. 392-396.

Whitby, K., et al., "Optimisation and Evaluation of a Quantitative Chemiluminescent Polymerase Chain Reaction Assay for Hepatitis C Virus RNA," (1995), *J. Virol. Methods*, 51, pp. 75-88.

Greer, C., et al., "PCR Amplification from Paraffin-embedded Tissues: Recommendations on Fixatives for Long-Term Storage and Prospective Studies", *PCR Methods and Applications* (Aug. 1991), vol. 1, pp. 46-50.

Van Den Brule, A., et al., "Rapid Detection of Human Papillomavirus in Cervical Scrapes by Combined General Primer-Mediated and Type-Specific Polymerase Chain Reaction", *Journal of Clinical Microbiology* (Dec. 1990), vol. 28, No. 12, pp. 2739-2743.

\* cited by examiner

FIG. 3
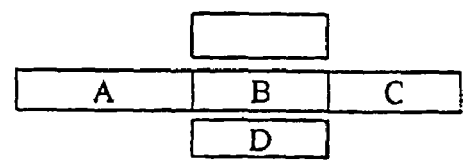 I
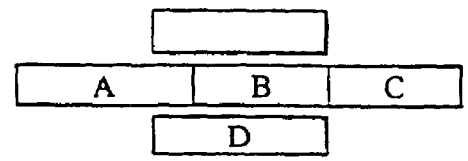 II
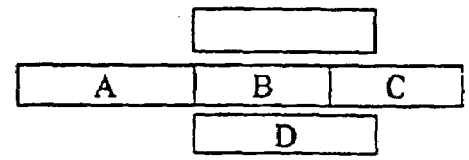 III
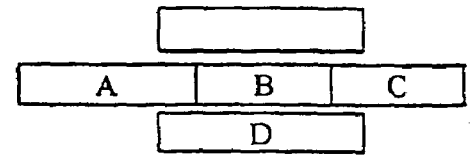 IV
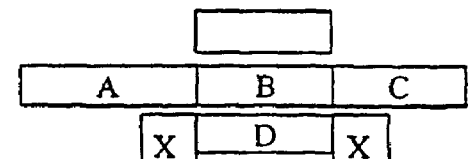 V
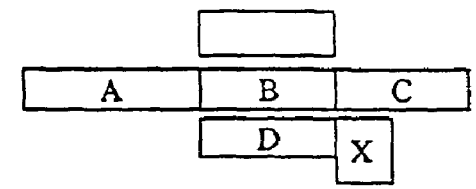 VI
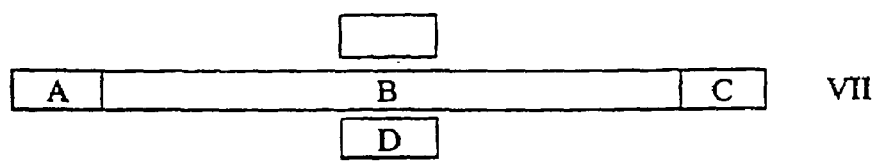 VII

FIG. 4

HCV      AGTATGAGTGTCGTGCAGCCTCCAGGACCCCCCCTCCCGGGAGAGCCA

HUMAN    AGTATGTGTGTCGTGCAGCCTCCAGGACCCCCACTCCCGGGAGAGCCA

FIG. 7

HCV:
5'-GTACTGCCTG ATAGGGTGCT TGCGAGTGCC CCGGGAGGTC TCGTAGACCG TGCACCATG-3

HGBV-B:
5'- GTACTGCCTG ATAGGGTCCT TGCGAGGGGA TCTGGGAGTC TCGTAGACCG TAGCACATG-3'

FIG. 5
$$1 + (n-1) \times 2 + m \times 3$$
1. n+m synthesis cycles
2. conc. ammonia
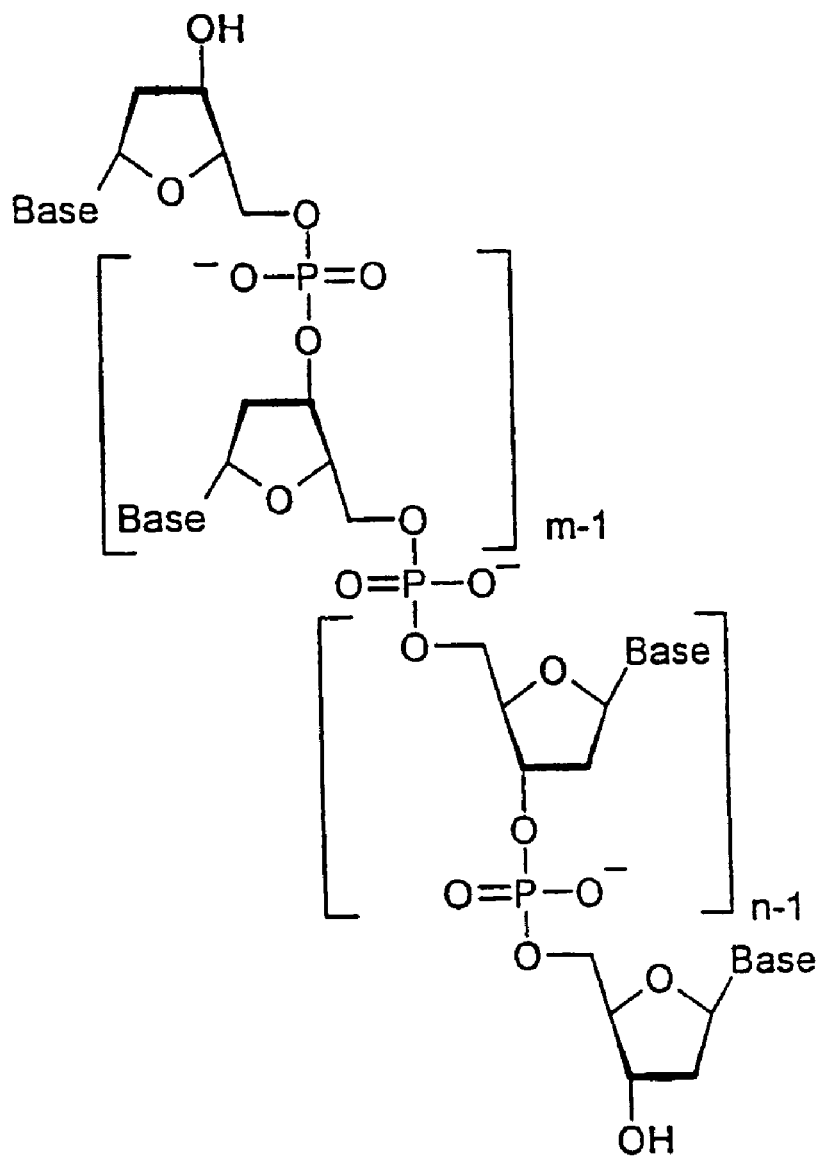

FIG. 6
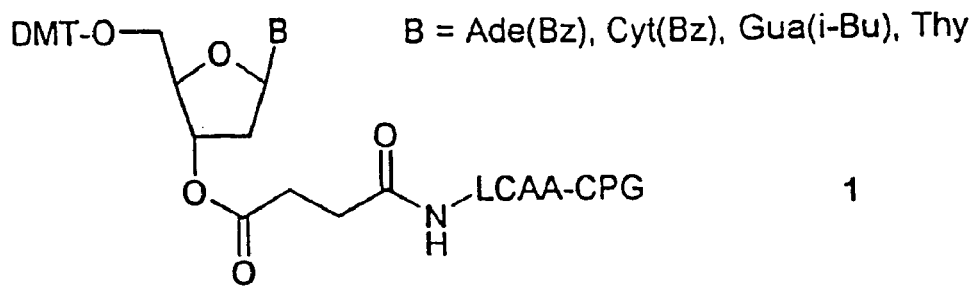
1
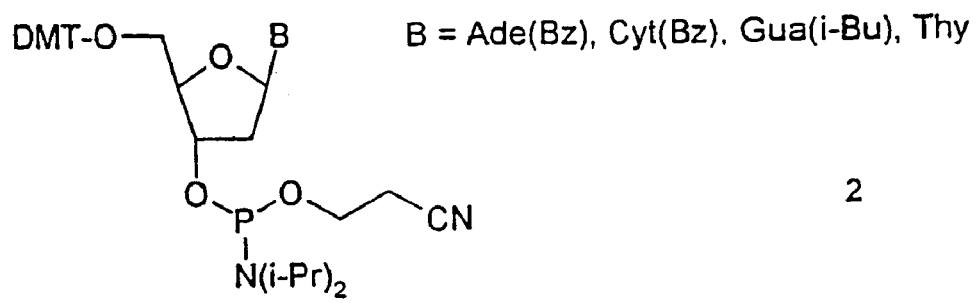
2
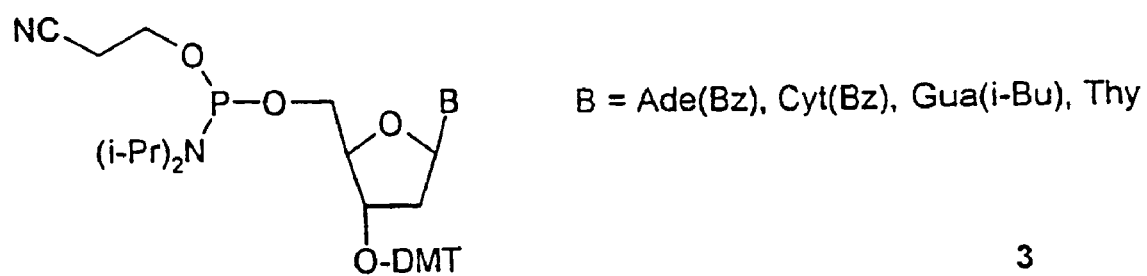
3

FIG. 8

```
HCVMCR01            AGTATGTGTGTCGTGCAGCC
MPF1                                    CCAGGACCCCCACTCCCGG
MPF1+1                                 TCCAGGACCCCCACTCCCGG
MPF2                                    CCAGGACCCCCACTCC
HCV_1A              AGTATGAGTGTCGTGCAGCCTCCAGGCCCCCCTCCCGGGAGAGCCA
HCV_1B              AGTATGAGTGTCGTGCAGCCTCCAGGCCCCCCTCCCGGGAGAGCCA
HCV_2B              AGTATGAGTGTCGTGCAGCCTCCAGGACCCCCTCCCGGGAGAGCCA
HCV_MCR             AGTATGTGTGTCGTGCAGCCTCCAGGACCCCACTCCCGGGAGAGCCA
MPR1_rev&compl              GTGTGTCGTGCAGCCTCCAGGA
MPR2_rev&compl                 TCGTGCAG

FIG. 9

HCV

261 5'-GGTACTGCCTGATAGGGTGCTTGCGAGTGCCCCGGAGGTCTCGTAGACCGTGCACCATGA-3' 333

| Primer | Sequence |
|---|---|
| Forward primer CK10/Reverse primer CK20 | 5'-CGTACTGCCTGATAGGGTGCT-3' / 3'-CAGAGMATMTGGMATCGTGTAMG-5' |
| Forward primer CK11/Reverse primer CK20 | 5'-CGTACTGCCTGATAGGGTGC-3' / 3'-CAGAGMATMTGGMATMGTGTAMG-5' |
| Forward primer CK10-1/Reverse primer CK20-1 | 5'-CGTACTGCCTIATAGGGTICT-3' / 3'-CDGDIMDTMTGGMATMGTGTAMG-5' |
| Forward primer CK11-1/Reverse primer ck20-1 | 5'-CGTACTGCCTIATAGGGTIC-3' / 3'-CDGDIMDTMTGGMATMGTGTAMG-5' |
| Forward primer CK10-2/Reverse primer CK20-2 | 5'-CGTAMTGMMTIATAGGGTIMT-3' / 3'-MDGDIMDTMTGGMAPPKPGTAM G-5' |
| Forward primer CK11-2/Reverse primer CK20-2 | 5'-CGTAMTGMMTIATAGGGTIM-3' / 3'-MDGDIMDTMTGGMAPPKPGTAM G-5' |
| Forward primer CK10/Reverse primer CK21 | 5'-CGTACTGCCTGATAGGGTGCT 3' / 3'-CITCAGAGCATCTGGCATCGTGTAC G-5' |
| Forward primer CK10-1/Reverse primer CK21-1 | 5'-CGTAMTGMMTIATAGGGTICT 3' / 3'-CITMDGDIMDTMTGGMATMGTGTAM G-5' |
| Forward primer CK11-1/Reverse primer CK21-1 | 5'-CGTAMTGMMTIATAGGGTIC 3' / 3'-CITMDGDIMDTMTGGMATMGTGTAM G-5' |
| Forward primer CK10-2/Reverse primer CK21-2 | 5'-CGTAMTGMMTIATAGGGTICT 3' / 3'-CIPMDGDIMDTMTGGMATMGTGTAM G-5' |
| Forward primer CK11-2/Reverse primer CK21-2 | 5'-CGTAMTGMMTIATAGGGTIC 3' / 3'-CIPMDGDIMDTMTGGMAPPRPGTAM G-5' |
| Forward primer CK10-2/Reverse primer CK21-3 | 5'-CGTAMTGMMTIATAGGGTIMT 3' / 3'-MIPMDGDIMDTMTGGMAPPKPGTAMG-5' |
| Forward primer CK11-2/Reverse primer CK21-3 | 5'-CGTAMTGMMTIATAGGGTIM 3' / 3'-MIPMDGDIMDTMTGGMAPPKPGTAMG-5' |

HGBV-B

389 5'-CGTACTGCCTGATAGGGTCCTTGCGAGGGATCTGGGAGTCTCGTAGACCGTAGCACATGC-3' 449

FIG. 10

SPECIFIC AND SENSITIVE NUCLEIC ACID DETECTION METHOD

This is a divisional of U.S. patent application Ser. No. 09/530,746, filed Nov. 16, 2000 now abandoned, which is the National Stage of International Application No. PCT/EP98/06952, filed Nov. 3, 1998, and which claims priority to German Patent Application Ser. Nos. 197 48 690.8, filed Nov. 4, 1997; 198 14 001.0, filed Mar. 28, 1998; and 198 14 828.3, filed Apr. 2, 1998; each of which is incorporated herein by reference in its entirety.

The invention concerns a method for detecting nucleic acids in which a section of these nucleic acids is amplified whereby this section must fulfil certain conditions with regard to its base sequence and it also concerns a reagent kit containing two primers and a probe which define this section.

One of the most frequently employed molecular-biological methods for detecting nucleic acids is hybridization with sequence-specific probes to detect homologous nucleic acid sequences. The detection of nucleic acid sequences is important for basic research but is of particular importance in various fields of application e.g. in the fields of medical diagnostics, forensic diagnostics, food diagnostics, environmental diagnostics, plant protection and veterinary medicine.

Either oligonucleotides (short DNA or RNA) or polynucleotides (longer DNA or RNA) are used as probes for this. An advantage of the shorter probes compared to the longer probes is that they have a better sequence selectivity due to the shorter hybridization region but they have the disadvantage of lower sensitivity. An improved sensitivity and sequence selectivity is achieved with PNA probes (peptide nucleic acids, e.g. WO 92/20702) since these probes have a higher binding affinity for nucleic acids (higher Tm) and are characterized by a higher base discrimination ($\Delta$Tm). Probes can additionally carry marker groups for nucleic acid detection which are suitable either for capturing and/or detecting hybrid complexes of the probe and nucleic acid to be detected.

In order to detect nucleic acids by hybridization, one or several probes are used either for hybridization in solution or on solid supports. Nucleic acid tests in solution are referred to as homogeneous test formats whereas tests on solid supports and/or mediated by solid supports are referred to as heterogeneous test formats. In the heterogeneous test format (e.g. dot blot) the nucleic acid to be detected can be pre-bound to the solid support. Hybridization is carried out by contact with a solution which contains the probe. Conversely, the probe can be pre-bound to the solid support (e.g. reverse dot blot). The hybridization is carried out by contacting the bound probe with a solution which contains the nucleic acid to be detected. Alternatively the complex of nucleic acid to be detected and probe can be firstly formed in solution and subsequently bound to the solid support. In homogeneous test formats probe pairs are for example used which carry terminal energy-transferring groups and are brought into direct contact by co-hybridization to the nucleic acid to be detected and thus generate a signal. Alternatively probes can also be used which, after binding to the nucleic acid to be detected, are converted from a quenched into an unquenched state by means of enzymatic 5' nuclease activity in solution.

The detection of nucleic acids solely by probe hybridization has only a limited sensitivity. Thus only a sensitivity in the pg to fg range is possible even when using sensitive detection marker groups such as $^{32}$P, digoxigenin, biotin, fluorescein, ruthenium chelates, fluorescein, rhodamine or AMCA. However, sensitivities in the ag range and a high test specificity is required for a sensitive nucleic acid test especially in the medical-diagnostic field. This applies to the detection of exogenous nucleic acids e.g. in the form of infectious pathogens as well as to the detection of the presence or absence or change of endogenous nucleic acids. A high test sensitivity and test specificity is, however, also very important in the other stated fields of application.

Thus some infectious pathogens such as e.g. HCV, HIV and HBV have to be detected even when there are only a few copies for a timely medical intervention e.g. by an early drug treatment. The detection of nucleic acid sequences of the pathogen is an advantage for such early tests for pathogens since a sensitive detection is already possible in an early phase of infection (latency phase) due to the availability of nucleic acid amplification methods (nucleic acid multiplication methods). The specific amplification of the agent to be detected is only possible in the case of nucleic acids but not in the case of immunological detection methods. In these methods an increase of the particles that are specific for the pathogen to be detected is only possible by means of the humoral immune response and formation of corresponding antibodies that are specific for the pathogens; however, this immune response only occurs after the latency period and it is a secondary reaction after infection by the pathogen. Therefore detection by means of nucleic acid hybridization has the advantage that the pathogen can be detected very sensitively directly after infection.

However, the success of medical intervention depends not only on being able to detect the pathogen at an early stage with high sensitivity but also very specifically. Therefore in order to treat specifically it is important to differentiate between various pathogens such as e.g. HAV, HBV, HCV, HIV, various herpes viruses, HPV and to differentiate between individual subtypes such as HIV-1 and HIV-2. In this connection it is also important to have quantitative information and no false-positive or false-negative results since such erroneous results can under certain circumstances have serious therapeutic consequences. This requires accuracy and high reproducibility of the results. Therefore the nucleic acid detection must not only be very sensitive but also very specific and reproducible. The specific and sensitive nucleic acid test must also be carried out rapidly so that specific treatment can begin immediately.

It is often also important to detect several pathogens such as e.g. HCV, HIV and HBV simultaneously e.g. as part of blood bank screening tests. In the current nucleic acid detection tests this is carried out by successive individual determinations of the pathogens to be detected. A disadvantage of this is that several determinations have to be carried out one after the other which is a particular disadvantage when screening a large number of specimens. The availability of sensitive and specific test methods which for example allow a rapid concurrent determination of several pathogens in parallel in a single sample (multiplex determination) is desirable for such nucleic acid determinations.

The availability of specific and sensitive nucleic acid detection methods is also advantageous for the detection of the presence or absence of endogenous nucleic acids within certain genomic loci and/or of changes thereof e.g. hereditary, spontaneous or a mixture of hereditary and spontaneous mutations, deletions, inversions, translocations, rearrangements or triplet expansions in the form of specific and/or polymorphous changes. However, the availability of specific and sensitive nucleic acid detection methods is not only very important in the medical sector but also in the other fields of applications mentioned above.

The previous test procedures for sensitively and specifically detecting the presence or absence of nucleic acids are based on combined nucleic acid amplification reactions (nucleic acid multiplication) and nucleic acid detection reactions (detection).

For this the nucleic acid to be detected is used in a form that is suitable for the amplification reactions e.g. in the form of untreated or treated sample material and/or sample material concentrates e.g. by adsorption of the untreated or treated sample material to the surface of a solid support and subsequent resorption from this solid support. Such solid supports are for example solid supports with glass-containing surfaces. These solid supports do not substantially purify and/or isolate the nucleic acids to be detected but only result in a concentration of the sample material and may lead to inactivation and/or elimination of inhibitors of the subsequent nucleic acid amplification and detection reactions. These solid supports also enable the provision of several nucleic acids to be detected e.g. in a multiplex method, in a form that is suitable for the nucleic acid amplification and detection reactions.

Other sample preparation methods include specific process steps for the nucleic acid-specific and/or sequence-specific binding of the nucleic acid to be detected e.g. by using solid supports with nucleic acid-specific binding groups and/or nucleic acid capture probes to selectively bind and release the nucleic acid to be detected by nucleic acid-specific binding and subsequent dissociation between the binding group and/or carrier-bound capture probe and nucleic acid to be detected. Nucleic acid specific binding groups and/or nucleic acid capture probes on the surface of the solid support are necessary for this type of solid support. Thus in order to prepare several nucleic acids to be detected e.g. for a multiplex method, it is either necessary to have several solid supports which is more complicated or to have solid supports with one or several binding groups and/or with multiple or several capture probes. Multiple capture probes contain several binding sequences for several nucleic acids to be detected. These supports with several binding groups and/or several and/or multiple capture probes are, however, more complicated to prepare. In addition it is more difficult to adjust the reaction conditions for the specific binding of several nucleic acids to be detected to a support containing several binding groups or/and capture probes or for binding several types of nucleic acids to be detected to a nucleic acid-specific binding group or to a capture probe with several complementary hybridization sequences.

The amplification and the detection of the prepared nucleic acids to be detected is carried out in heterogeneous or homogeneous nucleic acid amplification test formats. The nucleic acid amplification reactions and detection reactions can either be carried out successively (heterogeneous test methods) or simultaneously (homogeneous test methods). Target-specific nucleic acid amplification reactions, target-dependent signal-nucleic acid amplification reactions or signal nucleic acid amplification reactions are used as the amplification reactions. Detection systems for detecting amplified nucleic acids are either based on the incorporation of nucleotides and/or the use of labelled primers or labelled probes. The detection systems that are used contain either direct or indirect detection labels or coupled secondary and tertiary detection components. However, the amplified nucleic acids to be detected can also be detected by spectroscopic or physical methods.

The previous nucleic acid amplification detection method with integrated signal-nucleic acid amplification reactions have the disadvantage of lower sensitivity due to the non-exponential signal amplification, increased susceptibility to interference due to a stronger tendency for background signal generation as a result of the large number of probe components and the formation of unspecific detection signals since it is not the nucleic acid to be detected which is amplified target-independently but only a detection signal which is coupled thereto. Examples are coupled signal cascades (e.g. SELF cycle) or signal-generating probe tree or brush structures (e.g. branched DNA).

The previous nucleic acid amplification detection methods with integrated target-dependent signal-nucleic acid amplification reactions are more sensitive than the pure signal-nucleic acid amplification methods due to the exponential increase in signal, but they in turn have the disadvantage that unspecific detection signals are formed since it is not the nucleic acid to be detected as such that is enzymatically amplified in a target sequence-independent manner but only a detection signal derived in an initial target-dependent primary reaction in the form of a nucleic acid reporter molecule. Examples are the Qβ replication reaction in which a Qβ reporter molecule is amplified enzymatically or the ligase chain reaction in which sections of the nucleic acid reporter molecules are enzymatically linked in a sequence-independent manner.

The nucleic acid amplification products that have been generated by the previously most sensitive and specific exponential target-specific nucleic acid amplification reactions such as e.g. PCR (U.S. Pat. No. 4,683,202 or EP-B-0 202 362), RT-PCR, SDA, NASBA (EP-A-0 329 822) or TAM (WO 91/01384) were single or double-stranded nucleic acid amplification products produced by target sequence-dependent thermocyclic or isothermal enzymatic elongation of primers running in opposite directions that are sequence-specific for the nucleic acid to be detected and bind to the ends of the nucleic acid amplification unit (amplicon) of the deoxyribonucleic acids or ribonucleic acids to be detected or to complements thereof and thus restrict the nucleic acid amplification products. All four base specificities are incorporated in these elongation reactions.

The said nucleic acid amplification detection methods with an integrated target-specific nucleic acid amplification reaction are the most specific due to the target sequence-dependent enzymatic nucleic acid amplification cycles. Whereas linear target-specific nucleic acid amplification reactions such as e.g. the cycling probe reaction only lead to a limited sensitivity, exponential target-specific nucleic acid amplification reactions such as elongation-based reactions such as e.g. the polymerase chain reaction (PCR, RT-PCR, SDA) or transcription-based reactions such as e.g. nucleic acid sequence based amplification (NASBA) or transcription mediated amplification (TMA) have previously resulted in the most sensitive and specific signals.

Although mixed forms of target-dependent signal nucleic acid amplification and target-specific nucleic acid amplification such as e.g. the gap-filling ligase chain reaction (gap-filling LCR, WO 90/01069) have a target-dependent reaction step compared to the non-modified LCR, this is, however, restricted to limited sequence sections that are only composed of 1 or 2 base specificities and thus have a limited target specificity.

Various methods are available to detect the nucleic acid that is formed. Detection of the generated nucleic acid amplification products by means of fragment or sequence gel analysis is time-consuming and non-quantitative. Detection by means of carrier-bound dot, slot or reverse dot blot methods is also time-consuming and non-quantitative.

Sensitive and specific quantitative determinations of the nucleic acids to be detected have previously been possible in heterogeneous or homogeneous target-specific exponential nucleic acid amplification reaction formats in which the nucleic acid amplification product is captured in a part of the sequence section that is formed by elongation either by an incorporated label or by hybridization with a specific probe for the nucleic acid to be detected or its complement. Exponential nucleic acid amplification reaction formats in which an intercalation of nucleic acid binding dyes occurs are also sensitive but not sequence-specific.

In heterogeneous reaction formats the nucleic acid amplification product is bound to a solid support for example either by means of a primer capture modification or by means of an immobilized capture probe which is complementary to an internal sequence section of the nucleic acid amplification product and is detected as a result of incorporation of a detection-labelled nucleotide, by hybridization with a detection-labelled probe which is complementary to an internal sequence section of the nucleic acid amplification product or by means of a primer detection modification. In homogeneous reaction formats the detection has previously been carried out for example by hybridizing a probe which is complementary to an internal sequence section of the nucleic acid amplification product and which carries a quenched fluorescent label in which case there is a target sequence-dependent enzymatic abolition of the quenching by the primer elongation-dependent release of the quenched fluorescent labelled nucleotide (WO 92/02638) or by the attachment and/or intercalation of a detectable molecule or of a detectable group.

Nucleic acid amplification units (amplicons) have been used in all previous quantitative sensitive and specific heterogeneous and homogeneous target-specific exponential nucleic acid amplification reaction formats which have contained additional sequences of variable length between the flanking primer binding sequences and the internal probe binding sequence in addition to the specific primer and probe binding sequences. This five-part amplicon structure resulted in amplicon lengths that are larger than the sum of the sequence lengths of the two flanking primers and of the internal probe of between preferably 100 and 1000 base (pairs). Optimization of the nucleic acid amplification reaction by improved enzyme mixtures have previously been mainly directed towards longer nucleic acid amplification products.

Shorter amplicon lengths have previously been generated only for the detection of special sequences such as e.g. in triplet expansions, for in-situ examinations or the detection of greatly fragmented nucleic acids as part of age research. However, these short amplicon lengths were detected in time-consuming gel formats or in-situ formats which are characterized by poor sensitivity and/or lack of quantification. Other special short sequences such as short tandem repeats, short interspersed repetitive elements, microsatellite sequences or HLA-specific sequences have previously been only used as primer or probe binding sequences or in combination with other sequences.

The five part nucleic acid amplification products have the disadvantage that, in addition to the specific sequences that bind primers and probe, they have additional sequences which extend the amplicon and reduce the overall specificity with regard to the specificity-generating primer and probe binding reactions.

Previously used longer five-part nucleic acid amplification products have the additional disadvantage of longer primer elongation times and thus longer overall test times. The sensitivity is also limited by plateau effects of the participating enzymes and substrates which are reached earlier with longer amplicons. A further disadvantage of longer nucleic acid amplification products is an increased competition between the amplicon complementary strand and the detector or capture probe and thus a reduced sensitivity. A further disadvantage is the increasing chance of unspecific binding due to the additional sequences resulting in an increased background and thus lower sensitivity (lower signal-noise ratio). A further disadvantage when the nucleic acid amplification product is bound to carrier-bound capture probes is steric and kinetic hindrance of longer nucleic acid molecules; consequently nucleic acid amplification products of the former lengths have been preferably fragmented before binding to the capture probe. An additional disadvantage is the increased susceptibility to fragmentation within the amplicon sequence and thus destruction of the nucleic acid amplification unit; this leads to a lower reproducibility. An additional disadvantage is that longer nucleic acid amplification products hybridize less specifically at low test temperatures of e.g. 37° C. which are preset in conventional nucleic acid analyzers since there is a larger difference to the melting temperature. A further disadvantage of five part nucleic acid amplification products when detecting several different nucleic acid amplification products is that different nucleic acid amplification lengths are formed which make it more difficult to carry out a multiplex test.

The aim of the present invention was to provide an alternative detection method for nucleic acids which has advantages over the previously described methods.

A special object of the invention was to provide a target-dependent exponential nucleic acid amplification method for the highly sensitive, highly specific, reproducible and quantifiable detection of one or several single-stranded or double-stranded nucleic acids which in particular avoids one or several of the said disadvantages.

A further object of the invention was to make the selection of the primer and probe sequences so flexible that it is possible to determine several different nucleic acids to be detected in a standardized reaction format using primer or probe sequences that are preferably partially identical while retaining the overall specificity.

The invention concerns a method for the production of a plurality of amplificates of a section of this nucleic acid with the aid of two primers, one of which can bind to a first binding sequence (A) of a strand of the nucleic acid and the other can bind to a second binding sequence (C') which is complementary to a sequence C which is located in the 3' direction from A and does not overlap A, contacting the amplificates with a probe having a binding sequence D which can bind to a third sequence (B) located between the sequences A and C or to the complement (B') thereof, and detecting the formation of a hybrid of an amplificate and the probe wherein the third sequence (B) located between the binding sequences A and C or the complement (B') thereof contains no nucleotides that are not part of the sequence section E formed from the binding sequence D of the probe and the sequence of the amplificate bound thereto.

The invention also concerns a reagent kit for carrying out this method.

Figure 1:
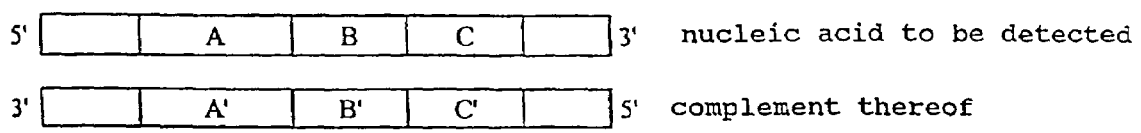
FIG. 1 shows schematically the notation used in the present description for the regions on the nucleic acid to be detected.

FIG. 3 shows schematically the arrangement of the binding sequences of the primers and probe in the present invention. There are various alternatives I to VI depending on whether and how the binding sequences overlap. Only one strand of the amplificate is shown in each case. The same arrangement (only complementary) can be constructed for a second strand of the amplificate. The picture is similar for the elongation products formed as intermediates. Cases V and VI show that, in addition to the binding sequence D, the probe contains additional regions X which can be the same or different and do not form base pairs with the amplificate. The prior art case is shown as VII for comparison; the sequences Z represent the additional sequences of the five part amplicon.

FIG. 4 shows sequences of the utilized regions i.e. A', B and C: HCV (SEQ ID NO: 6) and Human (SEQ ID NO: 7).

FIG. 5 shows schematically the synthesis of 5'-5-linked primers.

FIG. 6 shows the compounds used in FIG. 5.

FIG. 7 shows a particularly suitable region (SEQ ID NO: 8) of the HCV genome for performing the method according to the invention and a sequence from which the primer and probe sequences are preferably selected. This second sequence is taken from the non-human pathogenic virus HGBV-B (SEQ ID NO: 9). The selected primer and probe sequences are therefore sequences that are not specific for HCV (M. Med. Virol. 48, 60–67).

FIGS. 8 to 10 show preferred sequences for primers and probes for the HCV test: MPF1 (SEQ ID NO: 10), MPF1+1 (SEQ ID NO: 11), MPF2 (SEQ ID NO: 12), HCV_1A (SEQ ID NO: 13), HCV_1B (SEQ ID NO: 13), HCV_2B (SEQ ID NO: 6), HCV_MCR (SEQ ID NO: 7), MPR1_rev&comp1 (SEQ ID NO: 14), MPR2_rev&comp1 (SEQ ID NO: 15), HCVMCRO2_rev&comp1 (SEQ ID NO: 16), Forward primer CK10/Reverse primer CK20 with "C" designated at position 8 of the nucleotide sequence (SEQ ID NOs: 17 and 18), Forward primer CK11/Reverse primer CK20 with "M" designated at position 8 of the nucleotide sequence (SEQ ID NO: 19 and 20), Forward primer CK10-1 with "C" designated at positions 5, 8 and 9 of the nucleotide sequence/Reverse primer CK20-1 (SEQ ID NOs: 21 and 22), Forward primer CK11-1 with "C" designated at positions 5, 8 and 9 of the nucleotide sequence (SEQ ID NO: 23), Forward primer CK10-2/Reverse primer CK20-2 (SEQ ID NOs: 24 and 25), Forward primer CK11-2 (SEQ ID NO: 26), Reverse primer CK21 (SEQ ID NO: 27), Forward primer CK10-1 with "M" designated at positions 5, 8 and 9 of the nucleotide sequence/Reverse Primer CK21-1 (SEQ ID NOs: 28 and 29), Forward primer CK11-1 with "M" designated at positions 5, 8 and 9 of the nucleotide sequence (SEQ ID NO: 30), Reverse primer CK21-2 (SEQ ID NO: 31); Reverse primer CK21-3 (SEQ ID NO: 32), Forward primer CK12/Revrse primer CK22 (SEQ ID NOs: 33 and 34); Forward primer CK12-1/Reverse primer CK22-1 (SEQ ID NO: 35 and 36), Reverse primer CK22-2 (SEQ ID NO: 37), Reverse Primer CK22-3 (SEQ ID NO: 38), Forward primer CK12-2/Reverse primer CK22-4 (SEQ ID NOs: 39 and 40), Reverse primer CK22-5 (SEQ ID NO: 41), Reverse primer CK23 (SEQ ID NO: 42), Reverse primer CK23-1 (SEQ ID NO: 43), Reverse primer CK23-2 (SEQ ID NO: 44), Reverse primer CK23-3 (SEQ ID NO: 45), Reverse primer CK24 (SEQ ID NO: 46), Reverse primer CK24-1 (SEQ ID NO:. 47), Reverse primer CK24-2 (SEQ ID NO: 48), Reverse primer CK24-3 (SEQ ID NO: 49), HCV (SEQ ID NO: 93) and HGBV-B (SEQ ID NO: 94).

Nucleic acids which can be detected with the method according to the invention can be of any origin such as nucleic acids of viroidal, viral, bacterial or cellular origin or from yeasts or fungi. Samples (specimens) which contain the nucleic acid sequences to be detected or complements thereof are for example human, animal, bacterial or plant liquids or liquids from yeasts or fungi, excrements, smears, cell suspensions, cultures or tissue, cell or liquid biopsies. The nucleic acids are preferably present in solution. In order to realize the full advantages of the method according to the invention it has proven to be advantageous when the nucleic acid to be detected has a size of at least 40 bp. The nucleic acid can also be a nucleic acid prepared by cloning, amplification, or in vitro or in vivo replication.

The nucleic acid to be detected can be single-stranded (especially in the case of RNA) or double-stranded (especially in the case of DNA). In the case of double-stranded nucleic acids, both strands can be amplified or only one of them. Single or double-stranded amplificates can be formed from both types of nucleic acids and one or both can be used for the subsequent detection. The sequence of the probe or the probes is selected accordingly.

Positive or negative control nucleic acids or quantification standards which have been treated identically to the nucleic acids to be detected can be added to the sample or to a control sample. Suitable standards are for example internal or external, heterologous or homologous DNA or RNA standards containing probe binding sequences that are homologous to primer binding sequences or are heterologous to the sequences of the nucleic acids to be detected. Conversely it is also possible to use primer binding sequences that are heterologous especially in the 3' priming region and homologous probe binding sequences. Analogous specimens are preferably used as negative controls which do not contain the nucleic acids to be detected or complements thereof.

The sample is preferably subjected to one or several pretreatment steps before amplification in order to convert the nucleic acids to be detected into a form which can be amplified. In a first optional step the sample (specimen) is pretreated such that the sample is brought into a form from which the nucleic acid to be detected can be converted into a form suitable for converting the pretreated sample into a suitable form for amplification (e.g. separation of interfering components from the sample).

The type of sample pretreatment depends on the sample type and the complexity of the biological material in the sample. In the case of human body fluids such as e.g. human blood, blood cells are firstly separated in a preferred embodiment in order to produce plasma, serum or blood cell concentrates. This separation step and sample pretreatment considerably reduces the complexity of the biological sample material in the resulting fractions without substantially isolating the nucleic acid to be detected. In the case of sputum or smears the sample is pretreated for example by suspending the sputum or the smear in a liquid or in the case of urine for example by centrifuging and processing the fractions that are obtained. In the case of tissue biopsies the specimens are pretreated for example by suspension and treatment with an agent that dissolves the cell formations. Samples of cerebrospinal fluid are pretreated for example by centrifugation and processing the fractions obtained. In these cases the sample pretreatment also reduces the complexity of the biological sample material.

This can be followed by a step in which the nucleic acid to be detected from the pretreated sample is converted into a form that is suitable for amplification. Known methods are preferably used for this. In a preferred embodiment the pretreated sample is lysed in a first reaction step to release the nucleic acid to be detected e.g. by proteinase K treatment at elevated temperatures or by alkali in the case of deoxyribonucleic acids. In a second step the sample pretreated by lysis is concentrated by attachment to the surface of a solid support and subsequent resorption from this solid support after addition of chaotropic agents such as e.g. guanidinium hydrochloride or urea in the presence or absence of soluble alcohols such as e.g. isopropanol. Such solid supports are for example solid supports with glass-containing surfaces (e.g. magnetic particles, glass fleeces with glass-containing surfaces, particles, microtitre plates, reaction vessels, dip-sticks or miniaturized reaction chambers which can in turn also be a part of integrated reaction chips). These solid supports preferably result in a non-sequence specific purification i.e. there is not a substantial isolation of the nucleic acids to be detected from other nucleic acids but only a concentration of sample material (nucleic acids) and optionally an inactivation and/or elimination of inhibitors of the subsequent nucleic acid amplification and detection reactions. These solid supports also enable several nucleic acids to be provided in a form that is suitable for nucleic acid amplification and detection reactions e.g. as part of a multiplex method.

In another embodiment the nucleic acid to be detected from the pretreated sample can be converted after nucleic acid release in a first step by for example proteinase K treatment at elevated temperatures or by alkali in the case of deoxyribonucleic acids. In a second step the lysed pretreated sample is contacted with solid supports which are specifically modified with nucleic acid-specific binding groups and/or capture probes in order to selectively bind the nucleic acid to be detected and subsequently the bound nucleic acid to be detected is eluted again by dissociation between the binding group and/or carrier-bound capture probe and nucleic acid to be detected. Examples of nucleic acid-specific binding groups are PNA homopyrimidine oligomers such as e.g. $(T)_7$-PNA or nucleic acid-binding low molecular substances such as e.g. nucleic acid intercalators, major groove-binders or minor groove-binders. Examples of capture probes that are specific for the nucleic acid to be detected are nucleic acid oligomers or nucleic acid polymers that have binding sequences for one or several nucleic acids to be detected. Other examples of capture probes that are specific for the nucleic acid to be detected are PNA oligomers that have binding sequences for one or several nucleic acids to be detected. The nucleic acid-specific binding groups or the capture probes can be bound to the solid support with or without intermediate spacers either covalently or by means of binding pairs such as e.g. biotin:streptavidin or Ni:chelate.

The nucleic acid sequences used for amplification can be linear or circular and contain sequence modifications and/or other modifications such as e.g. natural or artificial nucleotide analogues or equivalents thereof or base analogues or equivalents thereof or can be methylated, capped, polyadenylated or modified by other means. The nucleic acids or complements thereof used for the amplification can be of natural origin, or they can be fragmented, modified or enzymatically, e.g. with the enzyme uracil deglycosylase (UNG), or physically pretreated, preamplified, or be produced chemically, photochemically or enzymatically e.g. by chemical oligonucleotide synthesis or in vitro replication, in vitro reverse transcription or in vitro transcription.

In the first essential step of the method according to the invention a segment of the nucleic acid to be detected is amplified. This segment is also referred to as an amplicon in the following. It is essential that this contains the sequence region between the outer ends of the binding sequences A and C' or of the complement thereof of the primers (the primer binding regions) and contains the binding region E of the probe or of the complement thereof. According to the present invention the amplicon (preferably the total length of the sequences of the regions A, B and C) is preferably shorter than 100 nucleotides, particularly preferably shorter than 60 nucleotides, but preferably longer than 40 nucleotides. However, this does not mean that the total length of the amplificates cannot be larger e.g. when the primers have additional nucleotides. Amplification methods are used which allow an amplification of the nucleic acid to be detected or the complement thereof and result in the formation of tripartite mini-nucleic acid amplification products [mini chain reaction (MCR)]. In principle all nucleic acid amplification methods that are known in the prior art can be used for this. Target-specific nucleic acid amplification reactions are preferably used. Theoretically exponentional target-specific nucleic acid amplification reactions are particularly preferably used in which an anti-parallel replication of the nucleic acid to be detected or of its complement is carried out e.g. elongation-based reactions such as the polymerase chain reaction (PCR for deoxyribonucleic acids, RT-PCR for ribonucleic acids) or transcription-based reactions such as e.g. nucleic acid sequence based amplification (NASBA) or transcription mediated amplification (TMA). Thermocyclic exponential elongation-based nucleic acid amplification reactions are particularly preferred such as e.g. the polymerase chain reaction. The nucleic acids to be detected or complements thereof which are used for the amplification can be present in the form of single-stranded or double-stranded deoxyribonucleic acids or ribonucleic acids. The aim of the amplification reaction (amplification) is to produce numerous amplificates of a segment of the nucleic acid to be detected. Hence an amplificate is understood as any molecular species produced by using sequence information of the nucleic acid. In particular the term refers to nucleic acids. The term "amplificate" includes single-stranded as well as double-stranded nucleic acids. In addition to the regions containing the sequence information of the underlying nucleic acid (amplicon), an amplificate can also contain additional regions which are not directly related to sequences of the nucleic acid to be amplified that are outside the ends of the primer binding sites which face away from another. Such sequences with a length of more than 15 nucleotides preferably do not occur on the nucleic acid to be detected or its complement and cannot hybridize with it by direct base pairing. Hence amplificates can either hybridize with the nucleic acid to be detected itself or with its complement. Amplificates are for example also products of an asymmetric amplification i.e. an amplification in which the two strands are formed in different amounts (e.g. by using different amounts of primers) or in which one of the two strands is subsequently destroyed (e.g. by RNase).

A primer in the sense of the present invention is understood as a molecule which can bind by means of base pairing to a nucleic acid T or its complement and which can be elongated preferably enzymatically. Oligo-nucleotides are preferred which can be elongated at their 3' end using the nucleic acid to be detected or a complement thereof as the template nucleic acid. Monovalent or multivalent or monofunctional or multifunctional agents can be used as primers which allow a nucleic acid-dependent elongation. These agents can also be composed of various types of molecules e.g. chimeras of PNA and nucleotide(s) or of protein/peptide and nucleotide(s). Preferred primers are oligomers or polymers with a binding length between 9 and 30 nt, especially preferably between 11 and 22 nt which bind anti-parallel to the nucleic acid T to be detected or its complement and which act as one of several reaction partners for an enzymatic replication of the nucleic acid to be detected or its complement. Oligomers are particularly preferably used as primers which, after adding an amplification regent, initiate a directed replication of one or both strands of the nucleic acid to be detected or of its complement by attachment of at least a part of the primer to the nucleic acid to be detected or to its complement. An example of a particularly preferred primer is an oligonucleotide with a free 3' hydroxyl end.

The agents used as primers can contain one or several binding sequences for one or several nucleic acids to be detected or complements thereof and can contain sequence modifications, terminal and/or internal sequence extensions and/or other modifications such as e.g. natural or artificial nucleotide analogues or equivalents thereof, non-functional nucleotide analogues or equivalents thereof or base analogues or equivalents thereof or they can be methylated, capped or polyadenylated or be modified in other ways. It is necessary that they have the required binding properties to the nucleic acid to be detected or its complement and can be elongated. Preferred nucleotide equivalents are PNA monomers or PNA oligomers (WO 92/20702) with or without positive and/or negative charges in the backbone and/or in the spacer. The agents used as primers can carry modifications which are either directly suitable for detection and/or binding to a solid support or are indirectly suitable via an additional binding pair.

Figure 2:
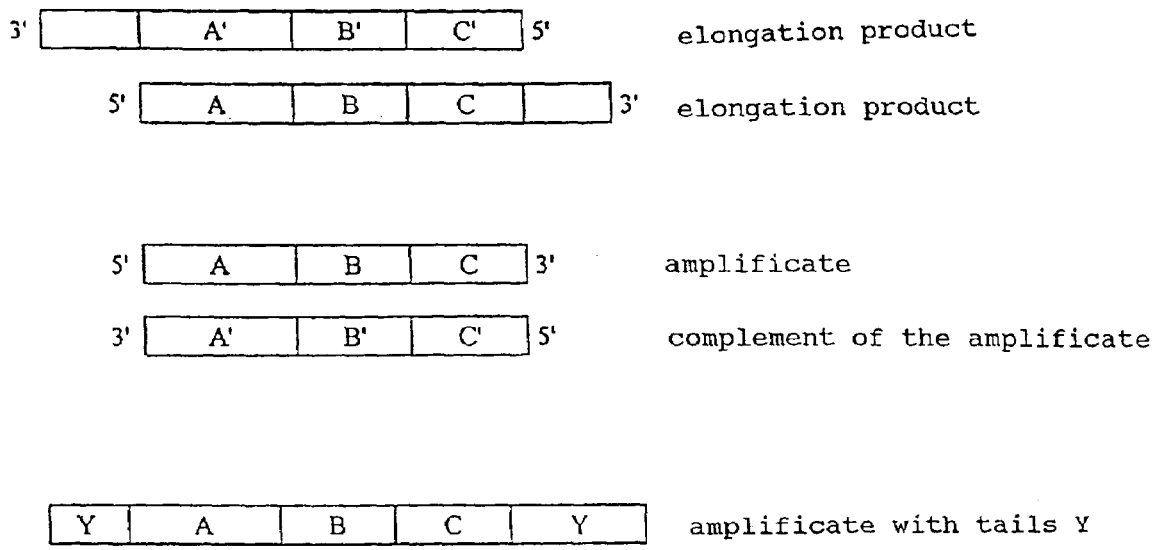
FIG. 2 shows the corresponding notation for the elongation products of the primers formed as intermediates as well as for the amplificates (amplicons). It also shows that the amplificates can have one or several additional regions Y which are outside the region that contains the sequence information derived from the nucleic acid to be detected.

Preferred primer modifications are fluorescent dyes e.g. fluorescein, rhodamine, AMCA or derivatives thereof, a partner in one of the binding pairs biotin:(strept)avidin, digoxigenin:anti-digoxigenin, digoxigenin:anti-digoxigenin coupled with aequorin, fluorescein:anti-fluorescein or ruthenium or rhenium-chelate or aequorin. Particularly preferred primer modification is biotin as a capture or detection modification. The primers can contain additional sequence regions Y especially at their 5' end (FIG. 2). In this case 5'-3' linkages as well as 5'-5' linkages and/or 5'-2' linkages are possible. Moreover they can have additional structural components such as spacers, immobilizable groups or solubility-mediating parts of the molecule or they can have regions that can be activated such as AP sites with regard to priming activity.

A probe is understood as a molecule which can hybridize with nucleic acids as a result of base-base interactions. Hence preferred probes are oligonucleotides and base-containing nucleic acid mimetics such as peptide nucleic acids (PNA). The length of a probe with reference to the binding sequence D is preferably between 9 and 30 bases.

PNA oligomer probes with or without positive or negative charges in the backbone and/or spacers have the additional advantage that they are resistant to degradation by nucleases or proteases due to the different structure of the backbone and of the H or $NH_2$ ends, have a higher melting point in binding complexes between nucleic acids and PNA than between two nucleic acid molecules and thus the hybrid complex is more stable, they can be used at low salt concentrations, there is a larger difference in the melting points in the case of mismatches and thus a better mismatch discrimination is possible, sequences with secondary structures are more accessible at low salt concentrations, competition between the amplicon opposite strand and probe is lower at low salt concentrations and thus a higher signal yield is achieved and the amplicon denaturing step can be potentially eliminated at low salt concentrations.

Monovalent or multivalent agents which allow a binding of amplification-dependent elongation products and/or amplified nucleic acid sequences can be used as probes. Oligomers or polymers can be preferably used as probes which bind anti-parallel to the nucleic acid to detected. Oligomers are particularly preferably used as probes which, as a result of the attachment of at least part of the probe to the nucleic acid to be detected or to its complement, result in a stable binding to one or both strands of the nucleic acid to be detected or to its complement in the subsequent reactions. The oligomers can contain 5'-3' linkages as well as 5'-5' linkages and/or 5'-2' linkages or additional structural components such as e.g. spacers or solubility-mediating parts of the molecule.

A binding sequence is preferably understood as the sequence of bases located between the outermost bases of a particular nucleic acid, primer or probe which bind to a particular nucleic acid, primer or probe via base-base interactions including these outermost bases.

The agents used as a probe can contain one or several binding sequences D for one or several nucleic acids to be detected or their complements and especially for one strand of the amplificate and can contain sequence modifications, terminal and/or internal sequence extensions and/or other modifications such as e.g. natural or artificial nucleotide analogues or equivalents thereof, non-functional nucleotide analogues or equivalents thereof or base analogues or equivalents thereof or they can be methylated, capped or poly-adenylated or be modified in other ways provided binding to one strand of the amplificate is possible. Preferred nucleotide equivalents are PNA monomers or PNA oligomers with or without positive and/or negative charges in the backbone and/or in the spacers. The agents used as probes can carry modifications which are either directly suitable for detection and/or binding to a solid support or are indirectly suitable via an additional binding pair. Preferred probe modifications (detectable groups L, immobilizable groups I) are fluorescent dyes e.g. fluorescein, rhodamine, AMCA or derivatives thereof, the binding pairs biotin:(strept)avidin, digoxigenin:anti-digoxigenin, digoxigenin:anti-digoxigenin coupled with aequorin, fluorescein:anti-fluorescein or ruthenium chelate or aequorin. Particularly preferred probe modifications are biotin as a capture or detection modification, digoxigenin, ruthenium or rhenium chelate or aequorin as detection modifications.

In the present invention the segment of the nucleic acid from which it is intended to produce a plurality of amplificates is selected such that it contains three regions A, B and C. Regions A and C are regions selected such that one primer can use sequence A as the binding sequence and the complement of the region C can serve as the binding sequence for the other primer. A complement within the sense of the present invention is understood as a nucleic acid or nucleic acid sequence which is essentially complementary to a certain other nucleic acid e.g. a sequence region e.g. of an amplificate or of the nucleic acid to be detected.

Essentially complementary means that the base pairs are selected such that (in the case of a hybridization with another-nucleic acid e.g. a probe or a primer) a hybridization can still occur under the test conditions or (in the case of an extension product of a primer relative to the template used) that it is possible to form the nucleic acid by a primer extension reaction using the corresponding nucleic acid. Hence essentially complementary often means that more than 90% of the bases of the nucleic acid or sequence in question can form base pairs with the certain nucleic acid or sequence under stringent conditions.

Regions A and C are preferably of sufficient length according to the invention that conditions can be found under which primers of a corresponding length can hybridize with bases in these regions. Hence the regions are preferably longer than 8, particularly preferably longer than 12 nucleotides. There are also preferred ranges in the sense of the invention with regard to the upper limit of the length of the regions A and C. Regions A and C are each preferably shorter than 30 and particularly preferably shorter than 20 nucleotides. In a special aspect of the invention the upper length of the regions is limited by the fact that the primers should be able to hybridize to them in an unspecific manner for the nucleic acid to be detected. Hence the particularly preferred length of the binding sequences A and C is 12 to 20 nucleotides. The regions A and C do not overlap on the nucleic acid to be detected. For the purposes of the invention the segment of the nucleic acid to be detected (which corresponds to the amplicon) and hence the amplificates that are formed from this contain a sequence B that is located between the regions A and C (FIGS. 1 to 3). This sequence has a length of one or several nucleotides, preferably more than 4, particularly preferably more than 8 nucleotides. The maximum length of sequence B is limited by the requirement that nucleotides should not be present which belong to the binding sequence of the probe and, in a particular aspect of the invention, by the desired unspecificity of the probe. Hence sequence B is preferably smaller than 30, particularly smaller than 15 nucleotides. Sequence B preferably has a length of between 4 and 30 nucleotides. The length of sequence B is particularly preferably between 8 and 15 nucleotides. This sequence or the complement thereof also serves to bind the probe for the purposes of the invention. The length of the probe is selected such that a hybridization with the amplificate is possible. The sequence of the probe is selected such that it contains a binding sequence D which is defined by the nucleotides of the probe which form base-base interactions with the amplicon and especially the nucleotides of the probe that have a base interaction with the outermost corresponding bases of the amplicon. The probe is essentially complementary to the nucleotides of the binding sequence E of the amplificate. The binding sequence D or its complement D' can be 100% complementary to the amplificate but also have mismatches between the outer ends of the binding sequence. In addition to the binding sequence, the probe can contain additional groups or residues or nucleic acid binding regions (FIG. 3, V, VI).

Various cases can be constructed depending on the length of the region B and the length of the binding sequence D or D'. In a first case the binding sequence D or D' is longer than the region B or B' of the amplicon. In this case the binding sequence D or D' extends into one or both regions A or A' and C or C' of the amplicon. These cases are shown in FIG. 3, II to IV. In these cases the amplificate contains no nucleotides between the ends of the regions A and C that face away from one another which do not belong to the binding sequence E or to the binding sequences of the primers. In FIG. 3, II and III the binding sequence D of the probe overlaps with one of the two binding sequences of the primers.

In a further case the length of the region B corresponds to the length of the region D such that the binding sequence of the probe does not overlap with the binding sequences of the primers (FIG. 3, I).

In a preferred embodiment the method according to the invention comprises the formation of three-part mini-amplicon (tripartite mini-amplicon) which apart from the sequences binding the primers and probe, have no additional sequences and thus avoid the disadvantages of forming longer nucleic acid amplification products while, on the other hand, the specificity of the overall amplification format is ensured by the binding of the primers, by the binding of the probe and by the course of the target-dependent enzymatic elongation reaction with all 4 nucleotide or base-specificities or natural or artificial analogues, isomers or equivalents thereof. The amplification method according to the invention is therefore also referred to as a mini-chain reaction (MCR).

If not stated otherwise in the following, the amplification of the nucleic acid sequences to be detected or their complements is carried out using the reaction steps and reaction conditions known to a person skilled in the art. One difference to conventional methods is the use of the specially selected primers and probe sequences which allow the formation and amplification of the tripartite mini-amplicons. An essential feature of the invention is the addition of one or several primers which bind to the primer binding sequences of the nucleic acid to be detected, of the tripartite mini-amplicon or to their complements.

It is common to add amplification reagents that enable amplification. Enzymatically active components (e.g. enzymes) in combination with elongation substrates and suitable auxiliary reagents (such as buffers) can be preferably used as amplification reagents. Preferred elongation substrates are nucleic acid building blocks or natural or artificial analogues or isomers or equivalents thereof. Agents are used as elongation substrates that are suitable for constructing the complementary strand of the nucleic acid to be detected. Nucleotides are preferably used as elongation substrates. Preferred nucleotides are dATP, dGTP, dCTP, dTTP and/or dUTP, dITP, iso-dGTP, iso-dCTP, deaza-dGTP and ATP, GTP, CTP, UTP and/or ITP, deazaGTP, iso-GTP, iso-CTP. Equivalents are PNA monomers or PNA oligomers with or without positive and/or negative charges in the backbone and/or in the spacer. As described above the elongation substrates can also carry modifications.

In the case of PCR the particularly preferred nucleic acid amplification reagents are mixtures of metastable or thermostable enzymatic DNA polymerase activities and mixtures of deoxyribonucleotides and/or ribonucleotides and suitable auxiliary reagents e.g. Taq-DNA polymerase in combination with dATP, dGTP, dCTP, dTTP and/or dUTP and auxiliary reagents such as e.g. salts and optionally detergents. Amplification reagents that are particularly preferably used in the case of RT-PCR are mixtures, complexes or domains of thermostable enzymatic reverse transcriptase and DNA polymerase activities and mixtures of deoxyribonucleotides and ribonucleotides and suitable auxiliary reagents e.g. mixtures of AMV or Mo-MLV reverse transcriptase or Tth-DNA polymerase in combination with dATP, dGTP, dCTP, dTTP and/or dTUP and ATP, GTP, CTP, UTP and auxiliary reagents such as e.g. salts and optionally detergents.

2-phase or 3-phase cycles and preferably 2-phase cycles are carried out for the thermocyclic amplification reactions (e.g. PCR, RT-PCR). In the 2-phase cycles the strand separation of the nucleic acid amplification products is carried out at a high temperature, preferably at 85° C.–95° C. , the common primer annealing and primer elongation is carried out at temperatures near to the melting point between the primer and elongation strand preferably between 52° C. and 75° C. The strand separation is carried out by supplying energy and/or enzymatically, preferably by an elevated temperature, microwaves or applying a potential via a microelectrode, particularly preferably by means of an elevated temperature. Up to 60 thermocycles are carried out and preferably 32–42 cycles. In the case of isothermal amplification reactions (e.g. SDA) a continuous incubation is carried out at an average temperature between 30° C. and 70° C. , preferably at 37° C.–45° C. with enzyme mixtures, complexes or domains or at 60° C.–65° C. with mesothermal enzyme mixtures, complexes or domains; in the case of SDA with e.g. mesothermal restriction endonucleases and DNA polymerases e.g. from *Bacillus stearothermophilus* (e.g. BsoBI/BstDNA-Pol exo); alternative enzymes are AvaI and BcaDNA-Pol exo. The incubation is carried out for up to 2 hours and preferably for 30–60 minutes. The amplification reaction can be carried out in reaction vessels, capillaries or miniaturized reaction chambers which can also be part of an integrated reaction chip.

When dUTP is used instead of or in addition to dTTP, dUMP instead of dTMP is incorporated by the DNA polymerase activity into the amplified nucleic acid sequence or its complement. This allows fragmentation of the amplification product and thus of its property as a nucleic acid amplification unit by incubation with the enzyme activity uracil deglycosylase, preferably with a thermolabile form of the enzyme activity in which the renaturation of the enzyme activity occurs more slowly after thermal denaturation. The UMP-containing amplification product can be incubated after the nucleic acid amplification and detection reaction (sterilization) and/or before a new nucleic acid amplification reaction (carry over prevention).

Psoralens and/or isopsoralens and derivatives thereof plus irradiation with UV light can be used alternatively to functionally inactivate the nucleic acid amplification product.

In the case of NASBA and TMA, mixtures, complexes or domains of enzymatic reverse transcriptase, DNA polymerase, RNase H and RNA polymerase and mixtures of deoxyribonucleotides and ribonucleotides and suitable auxiliary agents can be preferably used as nucleic acid amplification reagents, e.g. a mixture of AMV or Mo-MLV reverse transcriptase optionally *E. coli* DNA polymerase, optionally *E. coli* RNase H and T7, T3 or SP6-coding RNA polymerase or Mo-MLV reverse transcriptase and T7, T3 or SP6-RNA polymerase or appropriate mesostable enzymes e.g. from *Bacillus stearothermophilus* in combination with dATP, dGTP, dCTP, dTTP and/or dUTP and ATP, GTP, CTP, UTP and auxiliary agents such as e.g. salts and optionally detergents. The amplification reaction in the case of NASBA and TMA proceeds isothermally.

The formation of the amplificates is detected with the probe which binds to the binding sequence B of the amplicon to form a hybrid. The probe can act as a capture or detection probe. The ends of the binding sequence of the probe are between the outer ends of the primer binding sequences. The probe can thus hybridize with one strand of the amplificate.

Known conditions can be utilized for the probe binding since the method according to the invention is a special embodiment of the so-called hybridization tests which are known in outline to a person skilled in the field of nucleic acid diagnostics. Should experimental details not be elaborated in the following, complete reference is made to "Nucleic acid hybridization", editor B. D. Hames and S. J. Higgins, IRL Press, 1986, e.g. in chapters 1 (hybridization strategy), 3 (quantitative analysis of solution hybridization) and 4 (quantitative filter hybridization), Current Protocols in Molecular Biology, Ed. F. M. Ausubel et al., J. Wiley and Son, 1987 and Molecular Cloning, Ed. J. Sambrook et al., CSH, 1989. The known methods also include the chemical synthesis of modified and unmodified oligonucleotides and the selection of hybridization conditions which can achieve a specificity which, among others depends on the extent of homology between the nucleic acids to be hybridized, their GC content and their length.

For this purpose, if the capture probe (in a protected form) has not already been previously added, the probe is added to the reaction mixture after the amplification reaction preferably in the form of a solution. The reagent conditions are adjusted to allow hybridization of the probe with an amplificate.

Binding between the amplified nucleic acid sequence of the amplicon and/or its complement and the probe is preferably carried out at a constant temperature between 20° C. and 75° C. , preferably about 0° C.–30° C. , particularly preferably about 0° C.–15° C. below the melting temperature of the binding complex. The incubation period is up to 4 hours, preferably 15–120 minutes, particularly preferably 30–60 minutes. Binding to the amplificate and/or to its complement is carried out with or without a prior denaturing step. The reaction procedure without a prior denaturing step is preferably used for PNA oligomers with or without negative and/or positive charges in the backbone and/or in the spacer at low salt concentrations.

If several probes or multifunctional probes or probes which have several binding sequences for amplificates of various nucleic acids to be detected or their complements are used, it is possible to bind several different amplificates or complements thereof. In this case the formation of tripartite mini-amplicons preferably of a similar length and particularly preferably the formation of tripartite mini-amplicons of the same length allows uniform incubation conditions to be set in the nucleic acid amplification for the formation of the various binding complexes. This allows a concurrent and/or sequential detection of several nucleic acid sequences in a multiplex method. A multiplex amplification method is usually understood as a method in which either different sequences on a nucleic acid (e.g. different regions of a gene) or different sequences on different nucleic acids e.g. from different organisms e.g. different viruses are amplified simultaneously in one amplification mixture. Such methods make high demands on the reaction conditions since the amplifications for the various sequences must have a similar amplification efficiency for a reliable analysis. It is a subject matter of the present invention to exclude one of the factors causing differences in efficiency. For this purpose the amplicon lengths preferably do not differ by more than 20% and particularly preferably by not more than 5 nucleotides.

In a special embodiment of the multiplex method according to the invention, amplicons for the various sequences are prepared and subsequently the sum of the amplicons that are formed is determined. A detection method is preferably used for this in which one label can be used for all detections; thus for example all probes for the individual amplificates can be labelled identically e.g. with the same ruthenium complex. This procedure is particularly advantageous for testing samples from blood banks since it is not the type of infection which determines the suitability of the samples for blood donations, but rather the sample is already disqualified as blood donor material if any tested infection (e.g. HIV or HBV) is present.

In a multiplex amplification method one differentiates between genuine and non-genuine multiplex methods. In the case of non-genuine methods the primers are selected from strongly conserved regions of the analyte nucleic acids such that all nucleic acid sequences to be detected are amplified with one set of (2) primers. In genuine multiplex methods a mixture of more than 2 primers is used, of which at least 2 have a different selectivity. One or several of the primers can be specific for all or for a subset of the nucleic acids to be detected. This method is especially preferred when it is intended to concurrently amplify less related sequences.

Diverse combinations of nucleic acid sequences to be detected can be amplified concurrently by multiplex methods e.g. different subtypes of a virus or bacteria of various genera or species.

The binding complex formed between the amplificate and probe can be detected by methods known to a person skilled in the art, in particular in various embodiments, i.e. direct detection methods such as e.g. spectroscopic or physical methods, by sequencing or by heterogeneous or homogeneous test formats.

Direct spectroscopic or physical methods are for example melting temperature determinations, attachment of intercalating or nucleic acid binding dyes or metal atoms or particles, mass spectroscopy, surface plasmon resonance or fluorescence-coupled surface plasmon resonance or E-wave measurements.

The bound tripartite mini-amplicon can be sequenced by binding the primer and subsequent enzymatic sequencing according to Sanger. Either the primer or the chain termination reagents are preferably labelled in order to detect the sequencing products. The sequencing products can also be detected by mass spectroscopy. If only limited nucleotide types are added corresponding to the flanking nucleotides at the primer end, a mini-sequencing can be carried out which is especially advantageous for the analysis of polymorphisms.

In heterogeneous detection methods the probe can be used either as a capture probe or as a detector probe depending on the attached modification. If several probes are used it is possible to carry out multiplex formats.

If the probe is used as a capture probe, the probe can either be covalently prebound to the solid support or be prebound by means of a binding pair and the binding complex between the amplificate and the probe is formed on the solid support. In this embodiment, in addition to solid supports which contain only one type of probe, it is also possible to use supports which contain several or numerous types of probes such as e.g. probe beads or particles (so-called beads), probe test strips, probe panels or probe arrays on solid supports or miniaturized chips which in turn can also be a component of integrated reaction chips. These carrier-bound detection systems are particularly suitable for multiplex formats. In a preferred embodiment the complex between amplificate and capture probe is firstly pre-formed in solution and subsequently attached to the solid support. For this purpose the amplicon preferably contains an immobilizable group I which can bind to a group R located on a solid phase.

The type of solid phase depends on the group I which enables immobilization. It preferably has an immobilizing group R which can interact in a binding manner with I. If the immobilizable group is for example a hapten, a solid phase can then be used which has antibodies against this hapten on its surface. If the immobilizable group is a vitamin such as biotin, then the solid phase can contain immobilized binding proteins such as avidin or streptavidin. Biotin and streptavidin are particularly preferred residues I and R. Immobilization by means of a group on the modified nucleic acid is particularly advantageous since it can be achieved under milder conditions than for example hybridization reactions. In order to immobilize the nucleic acids that are formed it is preferable to fill the reaction mixture into a vessel whose surface can react with the immobilizable group either before, during or after formation of the nucleic acid hybrids. It is possible to use a solid phase in the form of a porous material such as a membrane, a fabric or a fleece on which the reaction mixture is applied. It is also possible to use beads e.g. magnetic particles or latex particles. The vessel is preferably a cuvette, a tube or a microtitre plate. The solid phase should have at least as many binding sites for the immobilizable group of the probe as there are nucleic acid hybrids and thus nucleic acids to be detected. The production of a preferred solid phase is described in EP-A-0 344 578 to the full contents of which reference is herewith made.

For the heterogeneous detection reactions the liquid phase is removed from the vessel, the porous material or from the pelleted beads after the incubation period during which the immobilization reactions takes place. The solid phase can subsequently be washed with a suitable buffer since the binding of the hybrids to the solid phase is very efficient. The bound binding complexes can be detected according to the prior art by means of the detection modification incorporated during the nucleic acid sequence amplification reaction in the primer and/or in a nucleotide and/or in the probe with the aid of known direct or indirect types of detection for these modifications.

In the case of detectable groups such as fluorescent labels, the amount of label can be determined fluorometrically. If the detectable group can be detected indirectly e.g. a hapten, the modified nucleic acid is preferably reacted with a labelled antibody against the hapten as described analogously in EP-A-0 324 474. The label on the antibody can for example be a coloured label or fluorescent label or preferably an enzyme label such as β-galactosidase, alkaline phosphatase or peroxidase. In the case of an enzyme label the amount of nucleic acid is measured by monitoring a reaction of the enzyme with a chromogenic, chemoluminogenic or fluorogenic substrate usually photometrically, chemoluminometrically or fluorometrically. The measured signal is a measure of the amount of nucleic acid to be detected that was originally present and thus for example of the organisms to be detected.

In a preferred embodiment the amplified tripartite mini-amplicons are bound by nucleic acid capture probes or PNA capture probes which are immobilized covalently on microtitre plates or magnetic particles. In this preferred embodiment the detection takes place, after formation of the binding complex and washing, by means of a biotin modification on one or both primers in the amplificate by attachment of avidin horseradish peroxidase and a mixture of TMB/TMF colour substrates.

In a further preferred embodiment a digoxigenin detection label is incorporated via one of the nucleotides of the nucleic acid amplification reaction. The binding complex between the amplificate and a biotin-labelled nucleic acid capture probe or PNA capture probe is bound on the surface of the streptavidin-coated reaction vessel. After washing, anti-digoxigenin-horseradish peroxidase antibody conjugates are attached and the colour test is carried out with the colour substrate ABTS.

In a further preferred embodiment one or several amplificates are detected after binding using one or several different covalently (e.g. anthraquinone: UV light coupling or gold surface: SH coupling) or coordinatively (e.g. biotin:streptavidin) bound capture probes, by washing and by detecting a fluorescent or chemiluminescent signal which has been either directly excited by primary light or by means of surface plasmon resonance or E-wave with the aid of e.g. CCD cameras or confocal fluorescent scanners.

If the probe is used as a detection probe, the probe can bind either at the same time as or before or after the amplificate binds to the solid phase. In this case the amplificate is bound to the solid phase by means of modifications which have been incorporated via one or both primers or via the incorporated nucleotides. Washing and detection are subsequently carried out.

In a further embodiment the complex between the amplificate and detection probe is firstly preformed in solution and subsequently attached to the solid support and washed. The solid phase-bound binding complexes between the amplificate and detection probe are detected by means of detection modification of the probe with the aid of known direct or indirect types of detection for these modifications according to the prior art.

In a preferred embodiment detection probes containing ruthenium chelate are bound to the amplificates which contain biotin modifications via one or both primers. The detection probes are either ruthenium-labelled oligonucleotides or ruthenium-labelled PNA oligomers. After formation of the binding complex between the ruthenium-labelled detection probe and biotin-labelled amplificate, the complex is bound to streptavidin-coated magnetic particles, transferred into a measuring cell, attached to an electrode within the measuring cell and an electrochemiluminescence signal is generated and measured.

The detection probe is labelled with digoxigenin in an additionally preferred embodiment. After formation of the binding complex between the digoxigenin-labelled detection probe and the biotin-labelled amplificate, the complex is bound by a capture probe which is immobilized covalently on a microtitre plate or on magnetic particles. After formation of the binding complex and washing, the detection is carried out in this preferred embodiment by means of a biotin modification of one or both primers in the tripartite mini-amplicon by attachment of avidin horseradish peroxidase and a mixture of TMB/TMF colour substrates.

When using homogeneous reaction formats, detection probes are used which carry either quenched fluorescent labels, internal base substitutions with double-stranded complex-activatable fluorescent dyes or terminal energy donors or acceptors (in combination with appropriate energy donors or acceptors on neighbouring primer or E-probe ends: energy transfer complexes). In these cases the detection probe is already added during the nucleic acid amplification. In the case of quenched fluorescent labels, fluorescent activation is accomplished by dequenching after binding the detection probe to the tripartite mini-amplicon that forms and exonucleolytic degradation and release of the nucleotide modified with the fluorescent dye. In the case of internal base substitutions, the fluorescent signal is generated by forming the binding complex between the detection probe and the tripartite mini-amplicon which forms. In the case of energy transfer complexes a fluorescent signal is formed by adjacent attachment of the labelled primer and the labelled probe. The resulting fluorescent signals are in each case measured preferably by real time measurements.

In a preferred embodiment fluorescein and rhodamine or derivatives thereof are used in the case of the quenched detector probes as fluorescent and quencher components. In a further embodiment ruthenium or rhenium chelates and quinones or derivatives thereof are used as electro-chemiluminescent and quencher components in the quenched detector probes. In a further preferred embodiment anthroquinone or derivatives thereof are used as internal base substituents of the detector probe. In a further embodiment Cy-5 and fluorescein or derivatives thereof are used as energy transfer components. In a special embodiment cyanine dyes such as e.g. SYBR green or acridine dyes are used.

Embodiments are particularly preferred in the sense of this first aspect of the invention in which at least one of the binding sequences of the primers and the probe is not specific for the nucleic acid to be detected. A sequence is specific in the sense of the invention when, as a result of a consecutive sequence of nucleobases, it would in principle be able to bind under stringent conditions only to one sequence on the nucleic acid to be detected but not to nucleic acids of other organisms or species or groups of organisms that are not to be detected. A sequence is preferably not specific for a sequence when it could hybridize with other nucleic acids under the conditions that are used to carry out the test.

Independent of the previously described first aspect of the invention, an overriding subject matter of the invention is a method for the specific detection of a nucleic acid comprising the steps of producing a plurality of amplificates of a segment of this nucleic acid with the aid of at least two primers, contacting the amplificates with a probe which can bind to the amplificate and detecting a hybrid formed from the strand of the amplificate and the probe, wherein at least one of the primers is not specific for the nucleic acid to be detected. In this case the region B can contain nucleotides which do not belong to the binding sequence E. However, in this case it is also possible that the binding sequences of the primer and the probe overlap.

Homologies to other genomes (sequences) can be identified with the aid of a defined initial sequence. A search engine with the name "BLAST" (basis local alignment search tool) that is accessible to anyone via the internet (homepage address:>http://www.ncbi.nlm.nih.gov/BLAST/<) can for example be used.

This enables access to diverse other sequence and protein data banks, the most important of which are:
genBank, EMBL, DDJB, PDB, PIR and Swiss-Prot.

BLASTN methods according to Altschul et al. (1990) J. Mol. Biol. 215: 403–410 using the UWGCG search method are also used.

The search procedures are also used for sequence data banks such as e.g. the EMBL sequence data banks and preferably also viral sequence data banks such as e.g. em-vrl.

The Blast program offers the user numerous adaptations to enable an individual search to be carried out i.e. to identify those sequences which are specific for one or several analytes or which are not specific i.e. which also occur in other organisms or not. In this connection reference is also made to Altschul, Stephen F., Warren Gish, Webb Miller, Eugene W. Myers, David J. Lipman (1990). Basic local alignment search tool, J. Mol. Biol. 403–410. Surprisingly the selectivity of the detection method is not solely derived from the selectivity of the individual primers for a specific target but rather from the cumulated selectivity of the overall system. Thus two primers or two primers and a probe may even be individually completely unselective i.e.

hybridize individually with numerous targets. However, since the selectivities of the individual primers and probes are (only) superimposed in the nucleic acid to be detected this results in an overall specificity. However, since the selectivity of the primers is not so firmly fixed when selecting the nucleic acid to be amplified and detected, it is much easier to localize short amplicons for different targets whose lengths completely or substantially (i.e. more than 95%) agree. This makes simultaneous amplifications and hybridizations (such as in the case of nucleic acid probe arrays) easier to achieve and reproduce.

The invention also concerns a reagent kit for carrying out this method. This contains the primers and preferably also a detection probe. However, it can also contain additional reagents such as buffers and enzymes e.g. a polymerase.

In a further embodiment the primers have additional sequences at their 5' end. These sequences are between 1 and 100 particularly preferably between 5 and 80 nucleotides long. It was previously unusual to select oligonucleotides with a length of more than 40 nt as primers. In one embodiment these sequences are selected such that they are just not able to hybridize with the nucleic acid at the primer binding site on the nucleic acid to be detected but can hybridize with another nucleic acid that is not to be detected. It is even possible to select these such that they are complementary to sequences which adjoin the binding site of the same primer on a nucleic acid that is not to be detected. Thus if the primer can also bind to a human genome, the sequences can also be human. It is possible to correspondingly modify one or even both of the primers. The additional sequences are not of such length that they would prevent the primers from hybridizing with the binding sequences on the nucleic acid to be detected e.g. the HCV genome. The additional sequences can also be selected such that they hybridize more firmly with short partial sequences of the primer in the primer binding site than with other sequences in the primer binding site. Hence, secondary structures within the primer can be solved and the ability of the primers to bind to the nucleic acid to be detected can be improved.

Another method of making the primers and probes specifically unselective is to use degenerate bases within the sequence. For this it is expedient to select the region in which the hybridization of the target nucleic acid with the primer or with the probe is to take place such that there are relatively few differences between the target sequence and another sequence which is not the sequence to be detected (e.g. of another microorganism). The differences which remain can be largely compensated by using degenerate bases at the differing base positions. Thus differences in the primers (A or G) can be compensated by incorporating the base P (6H, 8H-3,4-dihydro-pyrimido[9,5-C] [1,2]oxazin-7-one, e.g. Nucleic Acids Research, vol. 17, 24, 1989, p. 10373–10383). The same applies to pyrimidines where the base K is used (Nucleorides & Nucleotides, 16 (7–9), 1507–1511 (1997)). An even stronger degeneration is possible by using inosine (U.S. Pat. No. 5,585,477; U.S. Pat. No. 5,691,134; U.S. Pat. No. 5,578,467; J. Biol. Chem. 260, 5, 2605–2608, 1985; Nucl.Acids Res. 1995, 23, 13, 2499–2505) since inosine allows base pairing with all four bases.

A further method of using non-complementary bases is to replace A by D (diaminopurine) or/and to replace C by M (methylcytosine).

In a further embodiment the 5' end of one primer is linked covalently to the 5' end of the other primer.

Two different embodiments are conceivable for this. In a first embodiment the forward and the reverse primer are linked together for the amplification of the same analyte. Hence, the amplification results in numerous constructs in which two different amplificate strands are covalently linked together. Products are formed as a by-product, but could also be the basis of the test, in which only one of the two primer (parts) is elongated.

In a second embodiment the two linked primers are used to amplify different nucleic acids to be detected (e.g. one for HBV, the other for HGV). The corresponding reverse and forward primers must then be added for the amplification. In this case the 5' ends of the primer sequences can be directly linked together or via a linker. Any type of molecule can be used as a linker since it is not important to maintain a certain distance between the bases on a nucleic acid to be detected. However, the linker is preferably not so hydrophobic that it has an adverse effect on the solubility of the conjugate. The linker preferably contains one or several nucleotide sequences that are not directly complementary with the corresponding sequences or other sequences on the nucleic acid(s) to be detected. It is particularly preferred that at least one of the sequences is one which fulfil the conditions for the additional sequences of the (monofunctional) primers described above.

These (bifunctional) primer conjugates are thus also suitable for multiple (at least duplex) determinations of analyte nucleic acids. In principle these conjugates can be prepared in a known manner although it is preferable to firstly chemically synthesize the still unprotected individual sequences and then to activate one of the ends of an individual sequence and to de-protect one of the ends of the other individual sequence. The coupling reaction can proceed relatively automatically as a result of the activation group or it can be accelerated by activation reagents.

However, the conjugate is particularly preferably synthesized chemically by continuous sequential elongation on a solid phase without an interim detachment therefrom. For this the first partial sequence can be synthesized in the usual manner using 3'-phosphoramidites. A 5'-phosphoramidite is used instead of the 3'-phosphoramidite from the linkage site (5'-5' link) onwards. This leads to a reversal of the polarity within the conjugate. The reaction sequence is shown in FIG. 5 as an example and the reagents for this are shown in FIG. 6.

The primers preferably bind to the binding sequences A or C' as described above and the probe preferably binds to a region B located between the ends of the binding sequences A and C' or to the complement thereof.

Even if at least one sequence out of the 3 binding sequences of the two primers and the probe is not specific for the nucleic acid to be detected, the overall specificity of the detection method is retained. If one of the primer sequences is not specific for the nucleic acid to be detected but also binds to other nucleic acids, a specific nucleic acid amplification product cannot be formed on the other nucleic acid since the second primer binding sequence on this nucleic acid is absent. Unspecific nucleic acid amplification products are not detected on the other nucleic acid if the specific binding sequence for the probe is absent. If the second primer sequence is also not specific for the nucleic acid to be detected, then a specific nucleic acid amplification product can only be formed on the other nucleic acid if both primer binding sequences are in the same nucleic acid amplification unit. This nucleic acid amplification product is also not detected since the specific binding sequence for the probe is absent. If the probe sequence is not specific for the nucleic acid to be detected but both primers are specific, no nucleic acid amplification products of the other nucleic acid are formed. If, in addition to the probe sequence, one of the two primer sequences is also not specific for the nucleic acid to be detected, again no specific nucleic acid amplification product of the other nucleic acid can be formed. Unspecific nucleic acid amplification products of the other nucleic acid that may be formed contain other sequences in the probe binding region and are therefore not detected. If all three binding sequences for the two primers and the probe are not specific for the nucleic acid to be detected, no nucleic acid amplification product is formed if at least one of the two primer sequences is not located in a nucleic acid amplification unit of the other nucleic acid. If the probe sequence is not located in the nucleic acid amplification unit of the two primer sequences for the other nucleic acid, a specific nucleic acid amplification product of the other nucleic acid can indeed be formed but not detected. The only case in which a specific nucleic acid amplification product of the other nucleic acid can be formed and detected, is when all three sequences are within a nucleic acid amplification region. However, this can be avoided by appropriate selection of the sequences of the nucleic acid amplification unit, e.g. by not also selecting the primer hybridization sites from the same locus of the same organism that is not to be detected.

In a further embodiment the amplificates are produced using nucleotides, particularly preferably mononucleotides which are each complementary to A, G, C and/or T. The region B or B' of the nucleic acid to be detected preferably contains all 4 natural nucleobases.

In a further embodiment of the novel method partial components (primers or probes) of the various primer-probe combinations can be identical for the various nucleic acids to be detected. This enables the determination of several nucleic acid targets, e.g. for different viruses such as HBV, HIV and HCV, using a single amplification reaction (multiplex amplification). A technical advantage of the method according to the invention is that in multiple determinations of a sample a high degree of agreement of the measured values is achieved.

In the following the two aspects of the present invention are described on the basis of a HCV test. The nucleic acid sequence of HCV is for example described in EP-B-0 318 216. The sequences of its components are shown in FIG. 4. The method according to the invention enables a highly specific and highly sensitive detection of viral nucleic acids such as e.g. HCV-RNA from the 5' non-translated region of the HCV genome at a copy number of 10 copies per test with a dynamic range of $10^5$ due to an improved signal-noise ratio. This is surprising since primers and probes can be used in the test which do not have a primer/probe design that would be preferred by a person skilled in the art i.e. they have sequence sections that tend to form primer dimers or base mismatches near the 3' end. The short probe has a melting point near to the test temperature so that a person skilled in the art would not have expected a stable binding of the probe to the nucleic acid amplification product. In the previous tests using the longer, five-part nucleic acid amplification products it has previously not been attempted to increase the specificity and sensitivity by shortening the primer-probe sequences and/or the nucleic acid amplification product with the signal-generating component but rather elongating them.

Surprisingly it is possible to detect HCV-RNA specifically and reproducibly in positive HCV plasma samples in which the HCV-RNA was not sequence-specifically prepurified but was used directly from lysed plasma samples that were concentrated by means of glass surfaces despite the short amplified sequence of the nucleic acid to be detected. HCV-negative plasma samples result in no signal. This is surprising since the HCV-RNA genome is very susceptible to fragmentation in plasma lysates. The primers and probes that were used also give no signal with for example HIV plasma samples, HBV serum samples, chlamydia samples from urine or human DNA samples from whole blood which have also been concentrated by means of glass surfaces.

The method according to the invention can be used to avoid one or several of the disadvantages described for the prior art or to realize one or several of the following advantages. PCR cycles can be very much shorter. The overall time for the detection method can thus be shortened. The sensitivity of the test can be increased since less competition/displacement between the short complementary strand of the amplicon and the detection probe can take place. The specificity of the test is increased since the relative proportion of the internal detector region is increased in relation to the total amplicon. The ability to differentiate between subtypes can be increased. The test background can be reduced since short amplicons have less potential for unspecific hybridization. consequently the signal-noise ratio can be increased. The reproducibility of the results can be increased since smaller target regions on RNA genomes are less sensitive to RNA degradation. The potential for forming secondary structures is reduced.

The invention is elucidated in more detail by the following examples:

General

All oligonucleotides used are linear and single-stranded.

EXAMPLE 1

Detection of HCV from Human Blood a) Sample Preparation:

RNA was isolated from plasma using the following sample preparation protocol:
1. mix plasma (420 µl) with 80 µl proteinase K (25 mg/ml) and vortex for a few seconds
2. add 500 µl lysis buffer (incl. 1 µg carrier-RNA (polyA)/ml): 5.4 M guanidinium thiocyanate; 10 mM urea; 10 mM Tris-HCl; 20% Triton X 100; pH 4.4
3. vortex and subsequently shake for 10 min at RT
4. add 500 µl isopropanol-MGP (6 mg magnetic glass particles in isopropanol)
5. vortex and subsequently shake for 20 min at RT
6. magnetically separate the MGPs
7. remove and discard the supernatant
8. add 750 µl wash buffer: 20 mM NaCl; 20 mM Tris-HCl pH 7, 5; 70% ethanol
9. resuspend the MGPs on a vortex mixer and again separate magnetically
10. repeat wash process 5-times overall
11. add 100 µl DEMC water for the elution
12. shake for 15 min at 80° C.
13. separate magnetically
14. use 10 µl of the eluate in the RT-PCR b) Cloning and Preparation of the RNA Standard:

The wild-type standard "pHCV-wt" was firstly obtained by amplifying a section of the HCV genome using the primers KY80 (5'-gcagaaagcgtctagccatggcgt-3', SEQ.ID.NO. 1) and KY78 (5'-ctcgcaagcaccctatcagqcagt-3', SEQ.ID.NO. 2) and the amplicon was subsequently cloned into the vector pBluescript SK+ by means of a so-called blunt end cloning. The plasmid was isolated after growing the bacterial cells, it was linearized by restriction enzymatic digestion and the corresponding RNA fragment was obtained by in vitro transcription and purified.

The RNA was quantified by photometric measurement of the absorbence at 260 nm.

All the molecular biological methods described here can be taken from the relevant method books (e.g. Maniatis et al.; Ausubel et al.).

c) RT-PCR Assay:

The amplification was carried out using the reagents and cycler protocol mentioned above:

| reagents | final concentration in the master mix |
|---|---|
| 5 × RT-PCR-Puffer | 1 × |
| MnOAc | 2.5 mM |
| Tth-Polym. | 10 u |
| dNTP-Mix | 200 µM (dATP, dCTP, dGTP)/600 µM (dUTP) |
| UNG | 2 u |
| Primer forw. HC2F | 0.3 µM (5'-agtatgtgtgtcgtgcagcc-3', SEQ.ID.NO.3) |
| Primer rev. HC1F-bio | 0.3 µM (5'bio--tggctctcccgggagtgg-3', SEQ.ID.NO.4) |

The amplification was carried out according to the following cycler protocol:

| 10 min | 37° C. | decontamination by UNG |
|---|---|---|
| 30 min | 60° C. | reverse transcription |
| 1 min | 95° C. | denaturation |

| reagents | final concentration in the master mix |
|---|---|
| 35 cycles: | |
| 15 sec | 94° C. | denaturation |
| 20 sec | 56° C. | primer-annealing and elongation |
| 7 min | 72° C. | elongation |
| hold | 50° C. | | d) Detection:

The complete detection reaction was carried out fully automated on an Elecsys® 1010-analyzer (Boehringer Mannheim GmbH). Brief description:

1. remove 10 µl amplificate and 35 µl denaturating solution (BM-Id-No. 1469053)
2. incubate in a reaction vessel for 5 min at 37° C.
3. add 130 µl hybridization solution BM-Id-No. 146 9045 containing 25 ng/ml ruthenium-labelled probe
4. incubate for 30 min at 37° C.
5. add 35 µl of an Elecsys® SA magnetic bead solution (BM-Id-No. 171 9556)
6. incubate for 10 min at 37° C.
7. measure the electrochemiluminescence of 120 µl of the reaction mixture in the Elecsys® 1010 measuring cell Two different ruthenium-labelled probes were used for the hybridization:

```
PNA-probe:
Ru-(Ser)2-TCCAGGACCC-Ser-Gly      SEQ.ID.NO.5

DNA-probe:
5'-Ru-CTCCAGGCACCCC-3',
```

EXAMPLE 2

Determination of the Analytical Sensitivity on the Basis of an RNA Standard Dilution Series $10^1$, $10^2$, $10^3$, $10^4$ and $10^5$ copies of the HCV-RNA standard were amplified in duplicate determinations. A HCV-negative plasma, a HCV-positive plasma (after sample preparation) and water were used as controls. All probes were measured after amplification (ECL detection, Elecsys® 1010).

Result (Units×100):

| | PNA-probe | | DNA-probe | |
|---|---|---|---|---|
| template | 1st det. | 2nd det. | 1st det. | 2nd det. |
| RNA-Std. $10^5$ copies | 30608 | 30186 | 16791 | 15772 |
| RNA-Std. $10^4$ copies | 17895 | 15737 | 8977 | 7718 |
| RNA-Std. $10^3$ copies | 4137 | 4345 | 1911 | 1931 |
| RNA-Std. $10^2$ copies | 280 | 163 | 146 | 86 |
| RNA-Std. $10^1$ copies | 95 | 76 | 47 | 37 |
| HCV-positive plasma | 26658 | 26262 | 14996 | 14552 |
| HCV-negative plasma | 93 | 98 | 49 | 48 |
| water | 61 | 45 | 19 | 15 |

The use of the primer HC2F/HC1F-bio resulted in a very good amplification in the RT-PCR as measured by the signal level: the total detection range of the Elecsys ® was used (ca. 5 log steps).

There is a very good gradation of the signals within the dilution series.

The background measured with the HCV-negative plasma and water is relatively low.

PNA as well as DNA can be used as a probe.

EXAMPLE 3

Examination of the Specificity of the HCV Assay

Different starting nucleic acids (human genomic DNA; HIV-RNA; HBV-DNA, chlamydia-DNA) were tested using the primers and probes mentioned above. HCV plasma served as a positive control and HCV-negative plasma and water served as a negative control.

Result (Units×100):

| template | PNA-probe | | DNA-probe | |
| --- | --- | --- | --- | --- |
| | 1st det. | 2nd det. | 1st det. | 2nd det. |
| human genomic DNA from whole blood | 52 | 45 | 41 | 56 |
| HIV-positive plasma | 43 | 60 | 39 | 33 |
| HBV-positive plasma | 53 | 40 | 25 | 27 |
| chlamydia-positive urine | 43 | 34 | 19 | 17 |
| HCV-positive plasma | 11543 | 10644 | 6900 | 6348 |
| HCV-negative plasma | 65 | 67 | 45 | 40 |
| water | 29 | 25 | 15 | 15 |

Both probes (PNA, DNA) only resulted in a signal in the ECL measurement with their corresponding analytes. This means that there are no detectable unspecific amplifications with the primers and probes that are used.

EXAMPLE 4

Examination of the Probe Specificity

Different amplificates of other analytes were prepared for this experiment using the respective specific primers and then hybridized with the PNA and DNA probes described above. The corresponding analyte probe was used in each case to check the amplifications.

Result (Units×100): (In Each Case Average of Duplicate Determinations)

| template | PNA-probe for HCV | DNA-probe for HCV | HIV-probe | HBV-probe | chlamydia-probe |
| --- | --- | --- | --- | --- | --- |
| HIV | 13 | 6 | 11908 | nd | nd |
| HBV | 13 | 13 | nd | 1384 | nd |
| chlamydia | 10 | 10 | nd | nd | 3842 |
| HCV | 10132 | 9345 | nd | nd | nd |
| water | 13 | 9 | nd | nd | nd |

The control reactions (HIV, HVB, chlamydia) showed the clear detection of amplificate by the corresponding probe.
The PNA and DNA probes that were used only gave a specific signal with HCV.
No unspecific hybridizations of the PNA/DNA probes occurred with other amplificates.

EXAMPLE 5

Synthesis of a 5'-5'-linked oligonucleotide (3'-(primer-1)-5'-5'-(primer-2)-3'

The 5'-5'-linked oligonucleotide is synthesized on a DNA synthesizer model 394A from the Applied Biosystems Co. using the standard 1 µmol synthesis cycle recommended by Applied Biosystems. A synthesis column is used which contains 1 µmol of a support material (1) (obtainable from the Applied Biosystems Co.) functionalized with the corresponding 5'-O-DMT-protected start nucleoside and 5'-O-DMT-3'-phosphoramidite (2) (obtainable from the Applied Biosystems Co.) for the primer 1 sequence and 3'-O-DMT-5'-phosphoramidite (3) (obtainable from Eurogentec/Glen Research) for the primer 2 sequence. The synthesizer was stocked with the synthesis reagents recommended in the ABI manual (bottle #1–4=5'-O-DMT-3'-phosphoramidite 2 (0, 1 M in MeCN), #5–8=3'-O-DMT-5'-phosphoramidite 3 (0, 1 M in MeCN), #9 activator: tetrazole (0, 5 M in MeCN), #10 conc. ammonia p.A., #11 cap A: $Ac_2O$/pyridine/THF, #12 Cap B: N-methyl-imidazole/THF, #14, TCA in DCM (2%), #15 oxidation reagent: $I_2/H_2O$/pyridine/THF, #18 MeCN, #19 DCM) (all obtainable from the Applied Biosystems Co.). The progress of the synthesis is detected by regular trityl value determinations on the synthesizer (autoanalysis). After the synthesis cycle is completed it is followed by an automatic cleavage from the support using concentrated ammonia. The cleavage solution is fed into a special cleavage vessel on the synthesizer. This is then heated for 5 h in a water bath at 56° C. in order to cleave all protecting groups. After cooling the solution is concentrated on a rotary evaporator. The oligonucleotide is purified by preparative anion exchange HPLC on a protein Pak DEAE 8 HR 10×100 mm column (Waters) using 25 mM Tris/HC, 1 mM EDTA, 0–0.6 M NaCl, pH 8.5 as the elution buffer. It was analysed by a GenPak FAX 1.6×100 mm anion exchange HPLC column from the Waters Co. The product fractions are desalted by dialysis (MWCO 1000 from the Spectrapore Co.). The desalted oligonucleotide solution is rotary evaporated, dissolved in sterile water, filtered through a sterile 0.2 µm filter and the concentration is determined by UV spectroscopy at 260 nm. Yield: 75 OD

EXAMPLE 6

Alternative Primer and Probe Combinations

Alternatively primers and probes can be used from the following primer and probe regions:

forward primer: selected from the sequence between positions 390 and 417, reverse primer: selected from the sequence between positions 421 and 448, probe: selected from the sequence between positions 391 and 440 with reference to the HGBV-B sequence from sequence HG22304 obtainable from the EMBL data bank em-vrl or from Proc. Natl. Acad. Sci U.S.A. 1995, 92, 3401–3405 and/or from J. Virol. 69: 5621–5630. The sequence shown in FIG. 7 corresponds to positions 390 to 448 of this sequence so that the primer and probe positions can be directly converted.

Preferred primer/probe combinations are hence as follows:

forward primer selected from one of the sequences: 390–406, 390–408, 391–406, 391–408, 392–406, and 392–408, reverse primer selected from one of the sequences: 427–448, 427–447, 427–446, 428–448, 428–447, 428–446, 429–448 and 429–447, probe selected from one of the sequences: 402–412, 401–413, 400–414, 399–415, 398–415, 397–415, 396–415, 395–415, 394–415, 393–415, 392–415, 391–415, 408–436, 408–435, 408–434, 408–433, 408–432, 408–431, 408–430, 408–429, 408–428, 409–436, 409–435, 409–434, 409–433, 409–432, 409–431, 409–430, 409–429, 409–428, 410–436, 410–435, 410–434, 410–433, 410–432, 410–431, 410–430, 410–429, and 410–428, or preferably forward primer: sequence from 390–406, 390–408, 391–406, 391–408, 392–406, and 392–408, reverse primer: selected from one of the sequences: 423–448, 423–447, 423–446, 423–445, 423–444, probe: selected from one of the sequences: 402–412, 401–413, 400–414, 399–415, 398–415, 397–415, 396–415, 395–415, 394–415, 393–415, 392–415, 391–415, 409–433, 409–432, 409–431, 410–433, 410–432, , 410–431, 410–430, 410–429, 410–428, 409–430, 409–429, 409–428, 408–433, 408–432, 408–431, 408–430, 408–429, and 408–428 or particularly preferably:

forward primer: sequence from 390–406, 391–406, and 392–406, reverse primer: selected from one of the sequences: 423–448, 423–447, 423–446, 423–445, 423–444, probe: selected from one of the sequences: 402–412, 401–413, 400–414, 399–415, 398–415, 398–415, 397–415 396–415, 395–415, 394–415, 393–415, 392–415, 391–415, 409–433, 409–432, 409–431, 410–433, 410–432, 410–431, 410–430, 410–429, 410–428, 409–430, 409–429, 409–428, 408–433, 408–432, 408–431, 408–430, 408–429, and 408–428.

All these sequences are taken from the HGBV-B genome and therefore do not hybridize selectively with HCV.

EXAMPLE 7

Detection of HIV

A HIV-positive plasma with an initial concentration of 15000 genome equivalents (geq) HIV per ml served as the starting material. This plasma was successively diluted 10-fold in negative plasma and, after sample preparation, each was amplified in duplicate determinations with the corresponding primer pairs. A HIV-negative plasma and water served as controls. A HBV-positive and a HCV-positive plasma were also processed to determine the specificity. After amplification, all probes were measured (ECL detection, Elecsysol® 1010).

Primers and Probes That Were Used:

| primer | sequence | position | amplicon |
|---|---|---|---|
| SK 462 (SEQ ID NO: 50) | 5'-AGTTGGAGGACATCAAGCAGCCATGCAAAT-3' | 1359–1388 (30) | 142 bp |
| SK 431 (gag) (SEQ ID NO: 51) | 5'-TGCTATGTCAG1TCCCCTTGGTTCTCT-3' | 1474–1500 (27) | |
| SK 102 (SEQ ID NO: 52) | 5'-ATCAATGAGGAAGCTGCAGA-3' | 1402–1421 (20) | |
| RAR 1032 (SEQ ID NO: 53) | 5'-GAGACACCAGGAATTAGATATCAGTACAATGT-3' | 2961–2992 (32) | 169 bp |
| RAR 1033 (pol) (SEQ ID NO: 54) | 5'-CTAAATCAGATCCTACATATAAGTCATCCATGT-3' | 3097–3129 (33) | |
| RAR 1034 (SEQ ID NO: 55) | 5'-CCACAAGGATGGAAAGGATCACCAGCTATATITCCA-3' | 2997–3031 (35) | |
| GH A1F (SEQ ID NO: 56) | 5'-TGTACCAGTAAAATITAAAGCCAG | 2570–2592 (23) | 54 bp |
| GH A1R (pol) (SEQ ID NO: 57) | 5'-GGCCATTTGT1TAACTTTTGG | 2604–2623 (20) | |
| GH A1P (SEQ ID NO: 58) | 5'-AGGAATGGATGGC | 2591–2603 (13) | |
| GH A2F (SEQ ID NO: 59) | 5'-TACCTGGCATGGGTACCAGC | 4143–4162 (20) | 63 bp |
| GH A2R (pol) (SEQ ID NO: 60) | 5'-GACTAATITATCTACTTG1TCATTTTC | 4180–4205 (26) | |
| GH A2P (SEQ ID NO: 61) | 5'-CACACAAAGGAATI7GGAG | 4162–4179 (18) | |
| GH A3F (SEQ ID NO: 62) | 5'-TTTGQAATTCCCTACAATCC | 4644–4663 (20) | 59 bp |
| GH A3R (pol) (SEQ ID NO: 63) | 5'-AAYTCTTTATTCATAGATTCTACTAC | 4677–4702 (26) | |

-continued

| primer | | sequence | position | amplicon |
|---|---|---|---|---|
| GH A3P (SEQ ID NO: 64) | | 5'-CCCAAAGTCAAGGAG | 4663–4677 (15) | |
| GH A4F (SEQ ID NO: 65) | | 5'-TCAAAATITTCGGG1TTATTACAG | 4889–4912 (24) | 63 bp |
| GH A4R (SEQ ID NO: 66) | (pol) | 5'-AGCTTTGCTGGTCCTFITCCA | 4932–4951 (20) | |
| GH A4P (SEQ ID NO: 67) | | 5'-GGACAGCAGAAATCCACTT | 4913–4931 (19) | |
| GH A5F (SEQ ID NO: 68) | | 5'-GGAAAAGGTCTATCTGGCATGGGT | 4133–4156 (24) | 72 bp |
| GH A5R (SEQ ID NO: 69) | (pol) | 5'-ACTAATTTATCTACTTGTTCATTTCCTC | 4177–4204 (28) | |
| GH A5P (SEQ ID NO: 70) | | 5'-ACCAGCACACAAAGGAAITG | 4157–4176 (20) | |
| GH A6F (SEQ ID NO: 71) | | 5'-GCAACTAGATTGTACACA1TTAGAAG | 4412–4437 (26) | 74 bp |
| GH A6R (SEQ ID NO: 72) | (pol) | 5'-CTTCTATATATCCACTGGCTACATG | 4461–4485 (25) | |
| GH A6P (SEQ ID NO: 73) | | 5'-GAAAAGTTATCCTGGTAGCAGTT | 4438–4460 (23) | |

Note:
SK and RAP are each published Roche primer/probes, GH-A1 to GH-A6 are new MCR primers from the pol region of the HIV genome.

Amplification Mix and Thermocycle Protocol

Master mix

| Reagents | final conc. in master mix |
|---|---|
| 5× bicine buffer | 1× |
| MnOAc | 2.5 mM |
| dNTPs (incl. dUTP) | 200 μM/600 μM |
| forward primer | 0.3 μM |
| reverse primer (biotinylated) | 0.3 μM |
| Tth-polymerase | 10 units |
| UNG | 2 units |
| total volume: | 100 μl |

PCR-Cycling:

| | 10 min | 37° C. | UNG decontamination |
|---|---|---|---|
| | 30 min | 60° C. | reverse transcription |
| | 30 sec | 95° C. | denaturation |
| 5 cycles | 15 sec | 95° C. | denaturation |
| | 20 sec | 50° C. | annealing/elongation |
| 30 cycles | 15 sec | 94° C. | denaturation |
| | 20 sec | 60° C. | annealing/elongation |
| | 7 min | 72° C. | elongation |
| | | 50° C. | |

Result (ECL-Counts×100):

| template | SK-primer | RAR-primer | GH-A2 | GH-A3 | GH-A4 | GH-A6 |
|---|---|---|---|---|---|---|
| HIV 15000 copies/ml | 5763 | 294 | 5786 | 4209 | 7981 | 6809 |
| HIV 1500 copies/ml | 626 | 38 | 724 | 466 | 899 | 999 |
| HIV 150 copies/ml | 184 | 14 | 86 | 164 | 117 | 122 |
| HIV 15 copies/ml | 58 | 9 | 13 | 27 | 25 | 10 |
| HIV 1, 5 copies/ml | 49 | 9 | 14 | 32 | 14 | 10 |
| HIV-negative plasma | 70 | 9 | 22 | 38 | 16 | 11 |
| HCV-positive plasma | 49 | 9 | 5 | 58 | 16 | 10 |
| HBV-positive plasma | 37 | 9 | 5 | 81 | 17 | 10 |
| water | 12 | 9 | 16 | 35 | 15 | 10 |

There is a very good signal gradation within the dilution series.

EXAMPLE 8

Detection of HBV $10^0$, $10^1$, $10^2$, $10^3$, $10^4$ and $10^5$ genome equivalents (geq) HBV were amplified in duplicate determinations. A HBV-negative plasma and water served as controls. All probes were measured after amplification (ECL detection, Elecsys® 1010).

The sample preparation of HBV-positive plasma was carried out analogously to the sample preparation described for HCV.

Primers and Probes That Were Used:

| | primer/probe | sequence | position | amplicon length |
|---|---|---|---|---|
| Ref | HBV-Forward (SEQ ID NO: 74) | 5'-GGAGTGTGGATTCGCACT-3' | 2267–2284 (18) | 170 bp |
| | HBV-Reverse (SEQ ID NO: 75) | 5'-TGAGATCTTCTGCGACGC-3' | 2419–2436 (18) | |
| | capture probe (SEQ ID NO: 76) | 5'-AGACCACCAAATGCCCCTAT-3' | 2297–2316 (20) | |
| 1 | GHBV-1F (SEQ ID NO: 77) | 5'-CCACCAAATGCCCCTAT-3' | 2300–2316 (17) | 58 bp |
| | GHBV-1R (SEQ ID NO: 78) | 5'-CCCGTCGTCTAACAACAG-3' | 2340–2357 (18) | |
| | capture probe 1P (SEQ ID NO: 79) | 5'-CTTATCAACACTTCCGGAAACTA-3' | 2317–2339 (23) | |
| 2 | GHBV-2F (SEQ ID NO: 80) | 5'-GCGGGGTTTTTCTTGTT-3' | 203–219 (17) | 50 bp |
| | GHBV-2R (SEQ ID NO: 81) | 5'-TCTAGACTCTGCGGTATTGTG-3' | 232–252 (21) | |
| | capture probe 2P (SEQ ID NO: 82) | 5'-TTGACAAGAATCCTCA-3' | 218–233 (16) | |
| 3 | GHBV-3F (SEQ ID NO: 83) | 5'-GATCCCCAACCTCCAATC-3' | 315–332(18) | 61 bp |
| | GHBV-3R (SEQ ID NO: 84) | 5'-CAGCGATAACCAGGACAAAT-3' | 356–375 (20) | |
| | capture probe 3P (SEQ ID NO: 85) | 5'-ACTCACCAACCTCCTGTCCTCCA-3' | 333–355 (23) | |
| 4 | GHBV-4F (SEQ ID NO: 86) | 5'-ACTTCTTTCCTTCCGTCAGA-3' | 1965–1984 (20) | 61 bp |
| | GHBV-4R (SEQ ID NO: 87) | 5'-AAGGCTTCCCGATACAGAG-3' | 2007–2015 (19) | |
| | capture probe 4P (SEQ ID NO: 88) | 5'-GATCTCCTAGACACCGCCTCGG-3' | 1985–2006 (22) | |
| 5 | GHBV-F5 (SEQ ID NO: 89) | 5'-CAGCCAACCAGGTAGGAGTG-3' | 3014–3033 (20) | 55 bp |
| | GHBV-5R (SEQ ID NO: 90) | 5'-CCGTGTGGAGGGGTGAAC-3' | 3051–3068 (18) | |
| | capture probe 5P (SEQ ID NO: 91) | 5'-GGAGCATTCGGGCCAGG-3' | 3034–3050 (17) | |

Note: Ref. are reference primers, numbers 1–5 are the new MCR-HBV primers.

Amplication Mix and Thermocycler Protocol

Master mix

| reagents | final conc. in the master mix |
|---|---|
| 10× PCR buffer | 1× |
| MgCl$_2$ | 3 mM |
| dNTPs (incl. dUTP) | 200 μM/600 μM |
| forward primer | 0.3 μM |
| reverse primer (biotinylated) | 0.3 μM |
| Taq-polymerase | 2.5 units |
| UNG | 2 units |
| total volume: | 100 μl |

PCR-Cycling:

| | | | |
|---|---|---|---|
| | 10 min | 37° C. | UNG decontamination |
| | 10 sec | 95° C. | denaturation |
| 5 cycles | 10 sec | 55° C. | annealing |
| | 10 sec | 72° C. | elongation |
| | 10 sec | 90° C. | denaturation |
| 30 cycles | 10 sec | 60° C. | annealing |
| | 10 sec | 72° C. | elongation |
| | | 50° C. | |

The detection was also carried out analogously to the detection described for HCV.

Results (ECL-Counts×100):

| template | reference | GHBV-1 | GHBV-2 | GHBV-3 | GHBV-5 |
|---|---|---|---|---|---|
| HBV $10^5$ copies/ml | 3115 | 11079 | 37008 | 27190 | 37132 |
| HBV $10^4$ copies/ml | 2758 | 4849 | 10469 | 18181 | 9408 |
| HBV $10^3$ copies/ml | 1643 | 2433 | 2035 | 7166 | 2988 |
| HBV $10^2$ copies/ml | 226 | 357 | 302 | 235 | 493 |
| HBV $10^1$ copies/ml | 119 | 6 | 13 | 54 | 13 |
| HBV $10^0$ copies/ml | 14 | 11 | 13 | 146 | 13 |
| HBV-negative plasma | 15 | 12 | 11 | 85 | 14 |
| water | 15 | 11 | 15 | 44 | 11 |

The signals of the MCR primers show considerably improved dynamics in comparison to the reference.

There is a very good signal gradation within the dilution series.

The background measured on the HBV-negative plasma and water is relatively low.

SEQUENCE LISTING

<160> NUMBER OF SEQ ID NOS: 95

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence:
      amplification primer

<400> SEQUENCE: 1
gcagaaagcg tctagccatg gcgt                                              24

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence:
      amplification primer

<400> SEQUENCE: 2
ctcgcaagca ccctatcagg cagt                                              24

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence:
      amplification primer

<400> SEQUENCE: 3
agtatgtgtg tcgtgcagcc                                                   20

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence:
      amplification primer

<400> SEQUENCE: 4
tggctctccc gggagtgg                                                     18

<210> SEQ ID NO 5
<211> LENGTH: 12
<212> TYPE: DNA
<213> ORGANISM: Artificial Sequence
<220> FEATURE:
<223> OTHER INFORMATION: Description of Artificial Sequence: probe

<400> SEQUENCE: 5
ctccaggacc cc                                                           12

<210> SEQ ID NO 6
<211> LENGTH: 48
<212> TYPE: DNA
<213> ORGANISM: HCV

<400> SEQUENCE: 6
agtatgagtg tcgtgcagcc tccaggaccc ccctcccgg gagagcca                     48

```
<210> SEQ ID NO 7
<211> LENGTH: 48
<212> TYPE: DNA
<213> ORGANISM: Homo sapiens

<400> SEQUENCE: 7
agtatgtgtg tcgtgcagcc tccaggaccc ccactcccgg gagagcca                    48

<210> SEQ ID NO 8
<211> LENGTH: 59
<212> TYPE: DNA
<213> ORGANISM: HCV

<400> SEQUENCE: 8
gtactgcctg atagggtgct tgcgagtgcc ccgggaggtc tcgtagaccg tgcaccatg        59

<210> SEQ ID NO 9
<211> LENGTH: 59
<212> TYPE: DNA
<213> ORGANISM: HGBV-B

<400> SEQUENCE: 9
gtactgcctg atagggtcct tgcgagggga tctgggagtc tcgtagaccg tagcacatg        59

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence:
      amplification primer

<400> SEQUENCE: 10
ccaggacccc cactcccgg                                                    19

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence:
      amplification primer

<400> SEQUENCE: 11
tccaggaccc ccactcccgg                                                   20

<210> SEQ ID NO 12
<211> LENGTH: 16
<212> TYPE: DNA
<213> ORGANISM: Artificial Sequence
<220> FEATURE:
<223> OTHER INFORMATION: Description of Artificial Sequence:
      amplification primer

<400> SEQUENCE: 12
ccaggacccc cactcc                                                       16

<210> SEQ ID NO 13
<211> LENGTH: 48
<212> TYPE: DNA
<213> ORGANISM: Artificial Sequence
<220> FEATURE:
<223> OTHER INFORMATION: Description of Artificial Sequence:
      amplification primer

<400> SEQUENCE: 13
```
agtatgagtg tcgtgcagcc tccaggcccc ccctcccgg gagagcca         48

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence:
      amplification primer

<400> SEQUENCE: 14
gtgtgtcgtg cagcctccag ga                                    22

<210> SEQ ID NO 15
<211> LENGTH: 17
<212> TYPE: DNA
<213> ORGANISM: Artificial Sequence
<220> FEATURE:
<223> OTHER INFORMATION: Description of Artificial Sequence:
      amplification primer

<400> SEQUENCE: 15
tcgtgcagcc tccagga                                          17

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence:
      amplification primer

<400> SEQUENCE: 16
ccactcccgg gagagcca                                         18

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence:
      amplification primer

<400> SEQUENCE: 17
cgtactgcct gatagggtgc t                                     21

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence:
      amplification primer

<400> SEQUENCE: 18
gmatgtgcta mggtmtamga gac                                   23

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence:
      amplification primer

<400> SEQUENCE: 19
cgtactgcct gatagggttg c                                     21

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence:
      amplification primer

<400> SEQUENCE: 20
gmatgtgmta mggtmtamga gac                                              23

<210> SEQ ID NO 21
<211> LENGTH: 21
<212> TYPE: DNA
<213> ORGANISM: Artificial Sequence
<220> FEATURE:
<223> OTHER INFORMATION: Description of Artificial Sequence:
      amplification primer
<220> FEATURE:
<221> NAME/KEY: modified base
<222> LOCATION: 11,19
<223> OTHER INFORMATION: n=i

<400> SEQUENCE: 21
cgtactgcct natagggtnc t                                                21

<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence:
      amplification primer
<220> FEATURE:
<221> NAME/KEY: modified base
<222> LOCATION: 19
<223> OTHER INFORMATION: n=i

<400> SEQUENCE: 22
gmatgtgmta mggtmtdmnd gdc                                              23

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence:
      amplification primer
<220> FEATURE:
<221> NAME/KEY: modified base
<222> LOCATION: 11,19
<223> OTHER INFORMATION: n=i

<400> SEQUENCE: 23
cgtactgcct natagggtnc                                                  20

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence:
      amplification primer
<220> FEATURE:
<221> NAME/KEY: modified base
<222> LOCATION: 11,19
<223> OTHER INFORMATION: n=i

<400> SEQUENCE: 24
cgtamtgmmt nataggggtnm t                                    21

<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence:
      amplification primer
<220> FEATURE:
<221> NAME/KEY: modified base
<222> LOCATION: 19
<223> OTHER INFORMATION: n=i
<220> FEATURE:
<221> NAME/KEY: modified base
<222> LOCATION: 6,8,9
<223> OTHER INFORMATION: n=p

<400> SEQUENCE: 25
gmatgnknna mggtmtdmnd gdm                                   23

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence:
      amplification primer
<220> FEATURE:
<221> NAME/KEY: modified base
<222> LOCATION: 11,19
<223> OTHER INFORMATION: n=i

<400> SEQUENCE: 26
cgtamtgmmt nataggggtnm                                      20

<210> SEQ ID NO 27
<211> LENGTH: 26
<212> TYPE: DNA
<213> ORGANISM: Artificial Sequence
<220> FEATURE:
<223> OTHER INFORMATION: Description of Artificial Sequence:
      amplification primer

<400> SEQUENCE: 27
gcatgtgcta cggtctacga gacttc                                26

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence:
      amplification primer
<220> FEATURE:
<221> NAME/KEY: modified base
<222> LOCATION: 11,19
<223> OTHER INFORMATION: n=i

<400> SEQUENCE: 28
cgtamtgmmt nataggggtnc t                                    21

<210> SEQ ID NO 29
<211> LENGTH: 26
<212> TYPE: DNA
<213> ORGANISM: Artificial Sequence
<220> FEATURE:
<223> OTHER INFORMATION: Description of Artificial Sequence:
      amplification primer

```
<220> FEATURE:
<221> NAME/KEY: modified base
<222> LOCATION: 19
<223> OTHER INFORMATION: n=i

<400> SEQUENCE: 29
gmatgtgmta mggtmtdmnd gdmttc                                            26

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence:
      amplification primer
<220> FEATURE:
<221> NAME/KEY: modified base
<222> LOCATION: 11,19
<223> OTHER INFORMATION: n=i

<400> SEQUENCE: 30
cgtamtgmmt natagggtnc                                                   20

<210> SEQ ID NO 31
<211> LENGTH: 26
<212> TYPE: DNA
<213> ORGANISM: Artificial Sequence
<220> FEATURE:
<223> OTHER INFORMATION: Description of Artificial Sequence:
      amplification primer
<220> FEATURE:
<221> NAME/KEY: modified base
<222> LOCATION: 19
<223> OTHER INFORMATION: n=i
<220> FEATURE:
<221> NAME/KEY: modified base
<222> LOCATION: 24
<223> OTHER INFORMATION: n=p

<400> SEQUENCE: 31
gmatgtgmta mggtmtdmnd gdmntc                                            26

<210> SEQ ID NO 32
<211> LENGTH: 26
<212> TYPE: DNA
<213> ORGANISM: Artificial Sequence
<220> FEATURE:
<223> OTHER INFORMATION: Description of Artificial Sequence:
      amplification primer
<220> FEATURE:
<221> NAME/KEY: modified base
<222> LOCATION: 19
<223> OTHER INFORMATION: n=i
<220> FEATURE:
<221> NAME/KEY: modified base
<222> LOCATION: 6,8,9
<223> OTHER INFORMATION: n=p

<400> SEQUENCE: 32
gmatgnknna mggtmtdmnd gdmdtm                                            26

<210> SEQ ID NO 33
<211> LENGTH: 18
<212> TYPE: DNA
<213> ORGANISM: Artificial Sequence
<220> FEATURE:
<223> OTHER INFORMATION: Description of Artificial Sequence:
      amplification primer

<400> SEQUENCE: 33
```
cgtamtgmmt gatagggt                                              18

<210> SEQ ID NO 34
<211> LENGTH: 27
<212> TYPE: DNA
<213> ORGANISM: Artificial Sequence
<220> FEATURE:
<223> OTHER INFORMATION: Description of Artificial Sequence:
      amplification primer

<400> SEQUENCE: 34
gcatgtgcta cggtctacga gacttcc                                    27

<210> SEQ ID NO 35
<211> LENGTH: 18
<212> TYPE: DNA
<213> ORGANISM: Artificial Sequence
<220> FEATURE:
<223> OTHER INFORMATION: amplification primer
<220> FEATURE:
<221> NAME/KEY: modified base
<222> LOCATION: 11
<223> OTHER INFORMATION: n=i

<400> SEQUENCE: 35
cgtamtgmmt natagggt                                              18

<210> SEQ ID NO 36
<211> LENGTH: 27
<212> TYPE: DNA
<213> ORGANISM: Artificial Sequence
<220> FEATURE:
<223> OTHER INFORMATION: Description of Artificial Sequence:
      amplification primer
<220> FEATURE:
<221> NAME/KEY: modified base
<222> LOCATION: 13,19
<223> OTHER INFORMATION: n=i

<400> SEQUENCE: 36
gmatgtgmta mgntmtamna gamttmc                                    27

<210> SEQ ID NO 37
<211> LENGTH: 27
<212> TYPE: DNA
<213> ORGANISM: Artificial Sequence
<220> FEATURE:
<223> OTHER INFORMATION: Description of Artificial Sequence:
      amplification primer
<220> FEATURE:
<221> NAME/KEY: modified base
<222> LOCATION: 19
<223> OTHER INFORMATION: n=i
<220> FEATURE:
<221> NAME/KEY: modified base
<222> LOCATION: 24
<223> OTHER INFORMATION: n=p

<400> SEQUENCE: 37
gmatgtgmta mggtmtamna gamntmc                                    27

<210> SEQ ID NO 38
<211> LENGTH: 27
<212> TYPE: DNA
<213> ORGANISM: Artificial Sequence
<220> FEATURE:
<223> OTHER INFORMATION: Description of Artificial Sequence:
      amplification primer
<220> FEATURE:
<221> NAME/KEY: modified base

```
<222> LOCATION: 19
<223> OTHER INFORMATION: n=i
<220> FEATURE:
<221> NAME/KEY: modified base
<222> LOCATION: 24
<223> OTHER INFORMATION: n=p

<400> SEQUENCE: 38
gmatgtgmta mggtmtamna gamntmm                                 27

<210> SEQ ID NO 39
<211> LENGTH: 18
<212> TYPE: DNA
<213> ORGANISM: Artificial Sequence
<220> FEATURE:
<223> OTHER INFORMATION: Description of Artificial Sequence:
      amplification primer
<220> FEATURE:
<221> NAME/KEY: modified base
<222> LOCATION: 11
<223> OTHER INFORMATION: n=i

<400> SEQUENCE: 39
cgtdmtgmmt  ndtdgggt                                          18

<210> SEQ ID NO 40
<211> LENGTH: 27
<212> TYPE: DNA
<213> ORGANISM: Artificial Sequence
<220> FEATURE:
<223> OTHER INFORMATION: Description of Artificial Sequence:
      amplification primer
<220> FEATURE:
<221> NAME/KEY: modified base
<222> LOCATION: 13,19
<223> OTHER INFORMATION: n=i
<220> FEATURE:
<221> NAME/KEY: modified base
<222> LOCATION: 6,8,9,24
<223> OTHER INFORMATION: n=p

<400> SEQUENCE: 40
gmatgnknna mgntmtamna gamntmc                                 27

<210> SEQ ID NO 41
<211> LENGTH: 27
<212> TYPE: DNA
<213> ORGANISM: Artificial Sequence
<220> FEATURE:
<223> OTHER INFORMATION: Description of Artificial Sequence:
      amplification primer
<220> FEATURE:
<221> NAME/KEY: modified base
<222> LOCATION: 19
<223> OTHER INFORMATION: n=i
<220> FEATURE:
<221> NAME/KEY: modified base
<222> LOCATION: 6,8,9,24
<223> OTHER INFORMATION: n=p

<400> SEQUENCE: 41
gmatgnknna mggtmtamna gamntmm                                 27

<210> SEQ ID NO 42
<211> LENGTH: 27
<212> TYPE: DNA
<213> ORGANISM: Artificial Sequence
<220> FEATURE:
<223> OTHER INFORMATION: Description of Artificial Sequence:
      amplification primer
```

<400> SEQUENCE: 42
gcatgtgcta cggtctgcga gaactcc                    27

<210> SEQ ID NO 43
<211> LENGTH: 27
<212> TYPE: DNA
<213> ORGANISM: Artificial Sequence
<220> FEATURE:
<223> OTHER INFORMATION: Description of Artificial Sequence:
      amplification primer
<220> FEATURE:
<221> NAME/KEY: modified base
<222> LOCATION: 17
<223> OTHER INFORMATION: n=i

<400> SEQUENCE: 43
gmatgtgmta mggtmtnmga gaamtmc                    27

<210> SEQ ID NO 44
<211> LENGTH: 27
<212> TYPE: DNA
<213> ORGANISM: Artificial Sequence
<220> FEATURE:
<223> OTHER INFORMATION: Description of Artificial Sequence:
      amplification primer
<220> FEATURE:
<221> NAME/KEY: modified base
<222> LOCATION: 17
<223> OTHER INFORMATION: n=i

<400> SEQUENCE: 44
gmatgtgmta mggtmtnmga gakmtmc                    27

<210> SEQ ID NO 45
<211> LENGTH: 27
<212> TYPE: DNA
<213> ORGANISM: Artificial Sequence
<220> FEATURE:
<223> OTHER INFORMATION: Description of Artificial Sequence:
      amplification primer
<220> FEATURE:
<221> NAME/KEY: modified base
<222> LOCATION: 17
<223> OTHER INFORMATION: n=i
<220> FEATURE:
<221> NAME/KEY: modified base
<222> LOCATION: 6,8,9
<223> OTHER INFORMATION: n=p

<400> SEQUENCE: 45
gmatgnknna mggtmtnmga gakmtmm                    27

<210> SEQ ID NO 46
<211> LENGTH: 27
<212> TYPE: DNA
<213> ORGANISM: Artificial Sequence
<220> FEATURE:
<223> OTHER INFORMATION: Description of Artificial Sequence:
      amplification primer

<400> SEQUENCE: 46
gcatgtgcta cggtctgcga ggactcc                    27

<210> SEQ ID NO 47
<211> LENGTH: 27
<212> TYPE: DNA
<213> ORGANISM: Artificial Sequence
<220> FEATURE:
<223> OTHER INFORMATION: Description of Artificial Sequence:

```
    amplification primer
<220> FEATURE:
<221> NAME/KEY: modified base
<222> LOCATION: 17
<223> OTHER INFORMATION: n=i

<400> SEQUENCE: 47
gmatgtgmta mggtmtnmga ggamtmc                                              27

<210> SEQ ID NO 48
<211> LENGTH: 27
<212> TYPE: DNA
<213> ORGANISM: Artificial Sequence
<220> FEATURE:
<223> OTHER INFORMATION: Description of Artificial Sequence:
      amplification primer
<220> FEATURE:
<221> NAME/KEY: modified base
<222> LOCATION: 17
<223> OTHER INFORMATION: n=i

<400> SEQUENCE: 48
gmatgtgmta mggtmtnmga gkkmtmc                                              27

<210> SEQ ID NO 49
<211> LENGTH: 27
<212> TYPE: DNA
<213> ORGANISM: Artificial Sequence
<220> FEATURE:
<223> OTHER INFORMATION: Description of Artificial Sequence:
      amplification primer
<220> FEATURE:
<221> NAME/KEY: modified base
<222> LOCATION: 17
<223> OTHER INFORMATION: n=i
<220> FEATURE:
<221> NAME/KEY: modified base
<222> LOCATION: 6,8,9
<223> OTHER INFORMATION: n=p

<400> SEQUENCE: 49
gmatgnknna mggtmtnmga gkkmtmm                                              27

<210> SEQ ID NO 50
<211> LENGTH: 30
<212> TYPE: DNA
<213> ORGANISM: Artificial Sequence
<220> FEATURE:
<223> OTHER INFORMATION: Description of Artificial Sequence:
      amplification primer

<400> SEQUENCE: 50
agttggagga catcaagcag ccatgcaaat                                           30

<210> SEQ ID NO 51
<211> LENGTH: 27
<212> TYPE: DNA
<213> ORGANISM: Artificial Sequence
<220> FEATURE:
<223> OTHER INFORMATION: Description of Artificial Sequence:
      amplification primer

<400> SEQUENCE: 51
tgctatgtca gttccccttg gttctct                                              27

<210> SEQ ID NO 52
<211> LENGTH: 20
<212> TYPE: DNA
<213> ORGANISM: Artificial Sequence
```

```
<220> FEATURE:
<223> OTHER INFORMATION: Description of Artificial Sequence:
      amplification primer

<400> SEQUENCE: 52
atcaatgagg aagctgcaga                                                    20

<210> SEQ ID NO 53
<211> LENGTH: 32
<212> TYPE: DNA
<213> ORGANISM: Artificial Sequence
<220> FEATURE:
<223> OTHER INFORMATION: Description of Artificial Sequence:
      amplification primer

<400> SEQUENCE: 53
gagacaccag gaattagata tcagtacaat gt                                      32

<210> SEQ ID NO 54
<211> LENGTH: 33
<212> TYPE: DNA
<213> ORGANISM: Artificial Sequence
<220> FEATURE:
<223> OTHER INFORMATION: Description of Artificial Sequence:
      amplification primer

<400> SEQUENCE: 54
ctaaatcaga tcctacatat aagtcatcca tgt                                     33

<210> SEQ ID NO 55
<211> LENGTH: 35
<212> TYPE: DNA
<213> ORGANISM: Artificial Sequence
<220> FEATURE:
<223> OTHER INFORMATION: Description of Artificial Sequence:
      amplification primer

<400> SEQUENCE: 55
ccacaaggat ggaaaggatc accagctata ttcca                                   35

<210> SEQ ID NO 56
<211> LENGTH: 23
<212> TYPE: DNA
<213> ORGANISM: Artificial Sequence
<220> FEATURE:
<223> OTHER INFORMATION: Description of Artificial Sequence:
      amplification primer

<400> SEQUENCE: 56
tgtaccagta aaattaaagc cag                                                23

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence:
      amplification primer

<400> SEQUENCE: 57
ggccattgtt taacttttgg                                                    20

<210> SEQ ID NO 58
<211> LENGTH: 13
<212> TYPE: DNA
<213> ORGANISM: Artificial Sequence
<220> FEATURE:
```

<223> OTHER INFORMATION: Description of Artificial Sequence: probe

<400> SEQUENCE: 58
aggaatggat ggc                                                        13

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence:
      amplification primer

<400> SEQUENCE: 59
tacctggcat gggtaccagc                                                 20

<210> SEQ ID NO 60
<211> LENGTH: 26
<212> TYPE: DNA
<213> ORGANISM: Artificial Sequence
<220> FEATURE:
<223> OTHER INFORMATION: Description of Artificial Sequence:
      amplification primer

<400> SEQUENCE: 60
gactaattta tctacttgtt catttc                                          26

<210> SEQ ID NO 61
<211> LENGTH: 18
<212> TYPE: DNA
<213> ORGANISM: Artificial Sequence
<220> FEATURE:
<223> OTHER INFORMATION: Description of Artificial Sequence: probe

<400> SEQUENCE: 61
cacacaaagg aattggag                                                   18

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence:
      amplification primer

<400> SEQUENCE: 62
tttggaattc cctacaatcc                                                 20

<210> SEQ ID NO 63
<211> LENGTH: 26
<212> TYPE: DNA
<213> ORGANISM: Artificial Sequence
<220> FEATURE:
<223> OTHER INFORMATION: Description of Artificial Sequence:
      amplification primer

<400> SEQUENCE: 63
aattctttat tcatagattc tactac                                          26

<210> SEQ ID NO 64
<211> LENGTH: 15
<212> TYPE: DNA
<213> ORGANISM: Artificial Sequence
<220> FEATURE:
<223> OTHER INFORMATION: Description of Artificial Sequence: probe

<400> SEQUENCE: 64

```
cccaaagtca aggag                                              15

<210> SEQ ID NO 65
<211> LENGTH: 24
<212> TYPE: DNA
<213> ORGANISM: Artificial Sequence
<220> FEATURE:
<223> OTHER INFORMATION: Description of Artificial Sequence:
      amplification primer

<400> SEQUENCE: 65
tcaaaatttt cgggtttatt acag                                    24

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence:
      amplification primer

<400> SEQUENCE: 66
agctttgctg gtcctttcca                                         20

<210> SEQ ID NO 67
<211> LENGTH: 19
<212> TYPE: DNA
<213> ORGANISM: Artificial Sequence
<220> FEATURE:
<223> OTHER INFORMATION: Description of Artificial Sequence: probe

<400> SEQUENCE: 67
ggacagcaga aatccactt                                          19

<210> SEQ ID NO 68
<211> LENGTH: 24
<212> TYPE: DNA
<213> ORGANISM: Artificial Sequence
<220> FEATURE:
<223> OTHER INFORMATION: Description of Artificial Sequence:
      amplification primer

<400> SEQUENCE: 68
ggaaaaggtc tatctggcat gggt                                    24

<210> SEQ ID NO 69
<211> LENGTH: 28
<212> TYPE: DNA
<213> ORGANISM: Artificial Sequence
<220> FEATURE:
<223> OTHER INFORMATION: Description of Artificial Sequence:
      amplification primer

<400> SEQUENCE: 69
actaatttat ctacttgttc atttcctc                                28

<210> SEQ ID NO 70
<211> LENGTH: 20
<212> TYPE: DNA
<213> ORGANISM: Artificial Sequence
<220> FEATURE:
<223> OTHER INFORMATION: Description of Artificial Sequence: probe

<400> SEQUENCE: 70
accagcacac aaaggaattg                                         20
```

<210> SEQ ID NO 71
<211> LENGTH: 26
<212> TYPE: DNA
<213> ORGANISM: Artificial Sequence
<220> FEATURE:
<223> OTHER INFORMATION: Description of Artificial Sequence:
      amplification primer

<400> SEQUENCE: 71
gcaactagat tgtacacatt tagaag                                    26

<210> SEQ ID NO 72
<211> LENGTH: 25
<212> TYPE: DNA
<213> ORGANISM: Artificial Sequence
<220> FEATURE:
<223> OTHER INFORMATION: Description of Artificial Sequence:
      amplification primer

<400> SEQUENCE: 72
cttctatata tccactggct acatg                                     25

<210> SEQ ID NO 73
<211> LENGTH: 23
<212> TYPE: DNA
<213> ORGANISM: Artificial Sequence
<220> FEATURE:
<223> OTHER INFORMATION: Description of Artificial Sequence: probe

<400> SEQUENCE: 73
gaaaagttat cctggtagca gtt                                       23

<210> SEQ ID NO 74
<211> LENGTH: 18
<212> TYPE: DNA
<213> ORGANISM: Artificial Sequence
<220> FEATURE:
<223> OTHER INFORMATION: Description of Artificial Sequence:
      amplification primer

<400> SEQUENCE: 74
ggagtgtgga ttcgcact                                             18

<210> SEQ ID NO 75
<211> LENGTH: 18
<212> TYPE: DNA
<213> ORGANISM: Artificial Sequence
<220> FEATURE:
<223> OTHER INFORMATION: Description of Artificial Sequence:
      amplification primer

<400> SEQUENCE: 75
tgagatcttc tgcgacgc                                             18

<210> SEQ ID NO 76
<211> LENGTH: 20
<212> TYPE: DNA
<213> ORGANISM: Artificial Sequence
<220> FEATURE:
<223> OTHER INFORMATION: Description of Artificial Sequence: probe

<400> SEQUENCE: 76
agaccaccaa atgcccctat                                           20

<210> SEQ ID NO 77
<211> LENGTH: 17

```
<212> TYPE: DNA
<213> ORGANISM: Artificial Sequence
<220> FEATURE:
<223> OTHER INFORMATION: Description of Artificial Sequence:
      amplification primer

<400> SEQUENCE: 77
ccaccaaatg cccctat                                                        17

<210> SEQ ID NO 78
<211> LENGTH: 18
<212> TYPE: DNA
<213> ORGANISM: Artificial Sequence
<220> FEATURE:
<223> OTHER INFORMATION: Description of Artificial Sequence:
      amplification primer

<400> SEQUENCE: 78
cccgtcgtct aacaacag                                                       18

<210> SEQ ID NO 79
<211> LENGTH: 23
<212> TYPE: DNA
<213> ORGANISM: Artificial Sequence
<220> FEATURE:
<223> OTHER INFORMATION: Description of Artificial Sequence: probe

<400> SEQUENCE: 79
cttatcaaca cttccggaaa cta                                                 23

<210> SEQ ID NO 80
<211> LENGTH: 17
<212> TYPE: DNA
<213> ORGANISM: Artificial Sequence
<220> FEATURE:
<223> OTHER INFORMATION: Description of Artificial Sequence:
      amplification primer

<400> SEQUENCE: 80
gcggggtttt tcttgtt                                                        17

<210> SEQ ID NO 81
<211> LENGTH: 21
<212> TYPE: DNA
<213> ORGANISM: Artificial Sequence
<220> FEATURE:
<223> OTHER INFORMATION: Description of Artificial Sequence:
      amplification primer

<400> SEQUENCE: 81
tctagactct gcggtattgt g                                                   21

<210> SEQ ID NO 82
<211> LENGTH: 16
<212> TYPE: DNA
<213> ORGANISM: Artificial Sequence
<220> FEATURE:
<223> OTHER INFORMATION: Description of Artificial Sequence: probe

<400> SEQUENCE: 82
ttgacaagaa tcctca                                                         16

<210> SEQ ID NO 83
<211> LENGTH: 18
<212> TYPE: DNA
<213> ORGANISM: Artificial Sequence
<220> FEATURE:
```

-continued

<223> OTHER INFORMATION: Description of Artificial Sequence:
      amplification primer

<400> SEQUENCE: 83
gatccccaac ctccaatc                                                   18

<210> SEQ ID NO 84
<211> LENGTH: 20
<212> TYPE: DNA
<213> ORGANISM: Artificial Sequence
<220> FEATURE:
<223> OTHER INFORMATION: Description of Artificial Sequence:
      amplification primer

<400> SEQUENCE: 84
cagcgataac caggacaaat                                                 20

<210> SEQ ID NO 85
<211> LENGTH: 23
<212> TYPE: DNA
<213> ORGANISM: Artificial Sequence
<220> FEATURE:
<223> OTHER INFORMATION: Description of Artificial Sequence: probe

<400> SEQUENCE: 85
actcaccaac ctcctgtcct cca                                             23

<210> SEQ ID NO 86
<211> LENGTH: 20
<212> TYPE: DNA
<213> ORGANISM: Artificial Sequence
<220> FEATURE:
<223> OTHER INFORMATION: Description of Artificial Sequence:
      amplification primer

<400> SEQUENCE: 86
acttctttcc ttccgtcaga                                                 20

<210> SEQ ID NO 87
<211> LENGTH: 19
<212> TYPE: DNA
<213> ORGANISM: Artificial Sequence
<220> FEATURE:
<223> OTHER INFORMATION: Description of Artificial Sequence:
      amplification primer

<400> SEQUENCE: 87
aaggcttccc gatacagag                                                  19

<210> SEQ ID NO 88
<211> LENGTH: 22
<212> TYPE: DNA
<213> ORGANISM: Artificial Sequence
<220> FEATURE:
<223> OTHER INFORMATION: Description of Artificial Sequence: probe

<400> SEQUENCE: 88
gatctcctag acaccgcctc gg                                              22

<210> SEQ ID NO 89
<211> LENGTH: 20
<212> TYPE: DNA
<213> ORGANISM: Artificial Sequence
<220> FEATURE:
<223> OTHER INFORMATION: Description of Artificial Sequence:
      amplification primer

```
<400> SEQUENCE: 89
cagccaacca ggtaggagtg                                                    20

<210> SEQ ID NO 90
<211> LENGTH: 18
<212> TYPE: DNA
<213> ORGANISM: Artificial Sequence
<220> FEATURE:
<223> OTHER INFORMATION: Description of Artificial Sequence:
      amplification primer

<400> SEQUENCE: 90
ccgtgtggag gggtgaac                                                      18

<210> SEQ ID NO 91
<211> LENGTH: 17
<212> TYPE: DNA
<213> ORGANISM: Artificial Sequence
<220> FEATURE:
<223> OTHER INFORMATION: Description of Artificial Sequence: probe

<400> SEQUENCE: 91
ggagcattcg ggccagg                                                       17

<210> SEQ ID NO 92
<211> LENGTH: 10
<212> TYPE: DNA
<213> ORGANISM: Artificial Sequence
<220> FEATURE:
<223> OTHER INFORMATION: Description of Artificial Sequence: probe

<400> SEQUENCE: 92
tccaggaccc                                                               10

<210> SEQ ID NO 93
<211> LENGTH: 61
<212> TYPE: DNA
<213> ORGANISM: HCV

<400> SEQUENCE: 93
ggtactgcct datagggtgc ttgcgagtgc cccgggaggt ctcgtagacc gtgcaccatg        60
a                                                                        61

<210> SEQ ID NO 94
<211> LENGTH: 61
<212> TYPE: DNA
<213> ORGANISM: HGBV-B

<400> SEQUENCE: 94
cgtactgcct datagggtcc ttgcgagggg atctgggagt ctcgtagacc gtagcacatg        60
c                                                                        61

<210> SEQ ID NO 95
<211> LENGTH: 59
<212> TYPE: DNA
<213> ORGANISM: HGBV

<400> SEQUENCE: 95
gtactgcctg atagggtcct tgcgagggga tctgggagtc tcgtagaccg tagcacatg         59
```

The invention claimed is:

1. A method for the detection of several nucleic acids comprising the steps:
    (a) simultaneously producing in a multiplex reaction a plurality of amplificates of sections of the nucleic acids with the aid of pairs of two primers, of which in each case one can bind to a binding sequence (A'), which is essentially complementary to a sequence A of a strand of the nucleic acid, and of which the other can bind to a binding sequence C which is located in the 3' direction from A and does not overlap A, wherein the primers are selected such that the amplificates that are formed do not differ by more than 20% in length and are not longer than 100 nucleotides;
    (b) contacting the respective amplifcates with a probe that in each case has a binding sequence D or D', which can bind either to the sequence B located between the sequences A and C or to the complement thereof; and
    (c) detecting the formation of a hybrid of the amplificate and a probe;
    wherein the sequence located between the binding sequences A and C contains no nucleotides or less than 3 nucleotides that do not belong to the sequence section E formed from the binding sequence D of the probe and the sequence of the amplificate bound thereto and the amplificates are shorter than 100 nucleotides.

2. The method of claim 1, wherein amplificates of nucleic acids of HIV, HBV, and HCV are produced simultaneously.

3. The method of claim 1, wherein one of the pairs of two primers is selected from the group consisting of CK10 and CK20 (SEQ ID NOs: 17 and 18), CK11 and CK20 (SEQ ID NOs: 19 and 20), CK10-1 and CK20-1 (SEQ ID NOs: 21 and 22), CK11-1 and CK20-1 (SEQ ID NO: 23 and 22), CK10-2 and CK20-2 (SEQ ID NOs: 24 and 25), CK11-2 and CK 20-2 (SEQ ID NOs: 26 and 25), CK10 and CK21 (SEQ ID NOs: 17 and 27), CK10-1 and CK21-1 (SEQ ID NOs: 28 and 29), CK11-1 and CK21-1 (SEQ ID NOs: 30 and 29), CK10-1 and CK21-2 (SEQ ID NOs: 28 and 31), CK11-1 and CK21-2 (SEQ ID NOs: 30 and 31), CK10-2 and CK21-3 (SEQ ID NOs: 24 and 32), CK11-2 and CK21-3 (SEQ ID NOs: 26 and 32), CK12 and CK22 (SEQ ID NOs: 33 and 34), CK12-1 and 22-1 (SEQ ID NOs: 35 and 36), CK12-1 and 22-2 (SEQ ID NOs: 35 and 37), CK12-1 and CK22-3 (SEQ ID NOs: 35 and 38), CK12-2 and CK22-4 (SEQ ID NOs: 39 and 40), CK12-2 and CK22-5 (SEQ ID NOs: 39 and 41), CK12 and CK23 (SEQ ID NOs: 33 and 42), CK12-1 and CK23-1 (SEQ ID NOs: 35 and 43), CK12-1 and CK23-2 (SEQ ID NOs: 35 and 44), CK12-2 and CK23-3 (SEQ ID NOs: 39 and 45), CK12 and CK24 (SEQ ID NOs: 33 and 46), CK12 and CK24-1 (SEQ ID NOs: 33 and 47), CK12-1 and CK24-2 (SEQ ID NOs: 35 and 48), and CK12-2 and CK24-3 (SEQ ID NOs: 39 and 49).

4. The method of claim 1, wherein one of the pairs of two primers and one of the probes is selected from the group of primer pairs and probes consisting of primer pair SK462 and SK431 (SEQ ID NOs: 50 and 51), probe SK 102 (SEQ ID NO: 52); primer pair RAR1032 and RAR1033 (SEQ ID NOs: 53 and 54), probe RAR 1034 (SEQ ID NO: 55); primer pair GH A1F and GH A1R (SEQ ID NOs: 56 and 57), probe GH A1P (SEQ ID NO: 58); primer pair GH A2F and GH A2R (SEQ ID NOs: 59 and 60), probe GH A2P (SEQ ID NO: 61); primer pair GH A3F and GH A3R (SEQ ID NOs: 62 and 63), probe GH A3P (SEQ ID NO:64); primer pair GH A4F and GH A4R (SEQ ID NOs: 65 and 66), probe GH A4P (SEQ ID NO: 67); primer pair GH A5F and GH A5R (SEQ ID NOs: 68 and 9), probe GH A5P (SEQ ID NO: 70); and primer pair GH A6F and GH A6R (SEQ ID NOs: 71 and 72), probe GH A6P (SEQ ID NO: 73).

5. The method of claim 1, wherein one of the pairs of two primers and one of the probes is selected from the group of primer pairs and probes consisting of primer pair HBV-Forward and HBV-Reverse (SEQ ID NOs: 74 and 75), probe (SEQ ID NO: 76); primer pair GHBV-1F and GHBV-1R (SEQ ID NOs: 77 and 78), probe 1P (SEQ ID NO: 79); primer pair GHBV-2F and GHBV-2R (SEQ ID NOs: 80 and 81), probe 2P (SEQ ID NO: 82); primer pair GHBV-3F and GHBV-3R (SEQ ID NOs: 83 and 84), probe 3P (SEQ ID NO: 85); primer pair GHBV-4F and GHBV-4R (SEQ ID NOs: 86 and 87), probe 4P (SEQ ID NO: 88); and primer pair GHBV-5F and GHBV-5R (SEQ ID NOs: 89 and 90), probe 5P (SEQ ID NO 91).

6. The method of claim 1, wherein the amplificates are detected by means of mass spectroscopy.

7. The method of claim 1, wherein the step of contacting the respective amplificates with a probe D or D' is performed concurrently the step of producing the plurality of amplificates.

* * * * *